(12) United States Patent
Hossain et al.

(10) Patent No.: US 9,725,381 B2
(45) Date of Patent: Aug. 8, 2017

(54) FLUIDIZABLE CATALYSTS FOR OXIDATIVE DEHYDROGENATION OF HYDROCARBONS

(71) Applicant: King Fahd University of Petroleum and Minerals, Dhahran (SA)

(72) Inventors: Mohammad Mozahar Hossain, Dhahran (SA); AbdAlwadood Hassan Elbadawi, Dhahran (SA); Mohammed Saleh Ba-Shammakh, Dhahran (SA); Shaikh Abdur Razzak, Dhahran (SA)

(73) Assignee: King Fahd University of Petroleum and Minerals, Dhahran (SA)

(*) Notice: Subject to any disclaimer, the term of this patent is extended or adjusted under 35 U.S.C. 154(b) by 63 days.

(21) Appl. No.: 14/793,440

(22) Filed: Jul. 7, 2015

(65) Prior Publication Data

US 2017/0008821 A1    Jan. 12, 2017

(51) Int. Cl.
| | | |
|---|---|---|
| *C07C 5/333* | (2006.01) |
| *B01J 23/22* | (2006.01) |
| *B01J 21/06* | (2006.01) |
| *B01J 21/04* | (2006.01) |
| *B01J 35/10* | (2006.01) |
| *B01J 35/02* | (2006.01) |
| *B01J 35/00* | (2006.01) |

(52) U.S. Cl.
CPC ............ *C07C 5/3332* (2013.01); *B01J 21/04* (2013.01); *B01J 21/06* (2013.01); *B01J 23/22* (2013.01); *B01J 35/0026* (2013.01); *B01J 35/023* (2013.01); *B01J 35/1014* (2013.01); *C07C 2521/04* (2013.01); *C07C 2521/06* (2013.01); *C07C 2523/22* (2013.01)

(58) Field of Classification Search
CPC . B01J 23/22; B01J 21/04; B01J 21/066; B01J 35/023; B01J 35/1014; B01J 2523/55; C07C 5/3332; C07C 2521/04; C07C 2523/22
USPC .......................................... 502/350, 353, 354
See application file for complete search history.

(56) References Cited

U.S. PATENT DOCUMENTS

| | | | | |
|---|---|---|---|---|
| 2,261,159 | A | * | 11/1941 | Huppke ................... B01J 21/02 252/3 |
| 3,959,297 | A | * | 5/1976 | Ishioka .................... B01J 23/20 546/286 |
| 8,105,972 | B2 | | 1/2012 | Gaffney et al. |
| 2003/0166984 | A1 | * | 9/2003 | Park ...................... C07C 5/3332 585/444 |

(Continued)

OTHER PUBLICATIONS

"Structure and Properties of Vanadium Oxide-Zirconia Catalysts for Propane Oxidative Dehydrogenation," Andrei Khodakov et al. Journal of Catalysis 177 (1998), pp. 343-351.*

(Continued)

*Primary Examiner* — Patricia L Hailey
(74) *Attorney, Agent, or Firm* — Oblon, McClelland, Maier & Neustadt, L.L.P.

(57) ABSTRACT

Fluidizable catalysts for oxygen-free oxidative dehydrogenation of alkanes to corresponding olefins. The catalysts contain 10-20% (by weight per total catalyst weight) of one or more vanadium oxides as the catalytic material, which are mounted upon an alumina support that is modified with zirconia at alumina/zirconia ratios of 5:1 up to 1:2. Various methods of preparing and characterizing the fluidizable catalysts are also provided.

19 Claims, 16 Drawing Sheets

(56) References Cited

U.S. PATENT DOCUMENTS

2004/0166056 A1* 8/2004 Eyman .................. B01J 21/063
    423/652
2013/0317273 A1* 11/2013 Mondal .................. B01J 23/22
    585/661

OTHER PUBLICATIONS

"Effect of Mg and Zr Modification on the Activity of VOx/Al2O3 Catalysts in the Dehydrogenation of Butanes," M. E. Harlin et al. Journal of Catalysis 203 (2001), pp. 242-252.*

Komandur V.R. Chary, et al.; "Dispersion and reactivity of $V_2O_5$ catalysts supported on $Al_2O_3$-$ZrO_2$"; 2004; Catalysis Communications; pp. 479-484.

Sameer Ali Al-Ghamdi; "Oxygen-Free Propane Oxidative Dehydrogenation Over Vanadium Oxide Catalysts: Reactivity and Kinetic Modeling"; Dec. 2013; University of Western Ontario—Electronic Thesis and Dissertation Repository; 270 pp.

Mohammad Jakir Hossain, et al.; "Kinetic Modeling of Ethane Oxidative Dehydrogenation over VOx/Al2O3 Catalyst in Fluidized-Bed Riser Simulator"; Industrial and Engineering Chemistry Research; 1p.

Idris A. Bakare, et al.; "Fluidized bed ODH of ethane to ethylene over $VO_x$-$MoO_x/\gamma Al_2O_3$ catalyst: Desorption kinetics and catalytic activity"; 2014; Chemical Engineering Journal; pp. 1-10.

S. Al-Ghamdi, et al.; "$Vo_x/c$-$Al_2O_3$ catalyst for oxidative dehydrogenation of ethane to ethylene: Desorption kinetics and catalytic activity"; 2013; Applied Catalysis A: General; pp. 120-130.

* cited by examiner

FLUIDIZABLE CATALYSTS FOR OXIDATIVE DEHYDROGENATION OF HYDROCARBONS

STATEMENT OF ACKNOWLEDGEMENT

This project was funded by the National Plan for Science, Technology and Innovation (MAARIFAH)—King Abdulaziz City for Science and Technology—the Kingdom of Saudi Arabia, award number (ARP-30-252).

BACKGROUND OF THE INVENTION

Technical Field

The present invention relates to catalysts for oxidative dehydrogenation of hydrocarbons in a fluidized bed reactor. More specifically, the present invention relates to fluidizable, vanadium-based catalysts for oxidative dehydrogenation of alkanes.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Ethylene is a valuable feedstock for the petrochemical industry. It is used as a starting chemical to produce a wide range of chemicals and products [S. A. Mulla, O. V Buyevskaya, and M. Baerns, "A comparative study on non-catalytic and catalytic oxidative dehydrogenation of ethane to ethylene," vol. 226, pp. 73-78, 2002—incorporated herein by reference in its entirety]. Steam cracking of petroleum hydrocarbons is the conventional source of ethylene. Steam cracking processes are energy intensive, which contribute to the high ethylene production cost. The use of petroleum feedstocks is also a main source of energy in steam cracking, making it and even more costly approach for producing ethylene. On the other hand, oxidative dehydrogenation (ODH) has the potential to produce ethylene from relatively cheaper gaseous feedstocks such as natural gas and refinery gas. The use of a suitable catalyst can efficiently process the gaseous feeds to produce ethylene.

Due to its potential, in recent years, ODH research has received a great deal of attention, both in the industrial and academic settings. As a result, the development of a suitable catalyst, that maximizes the ethylene selectivity, and minimizes the carbon dioxide formation, is most relevant for the successful implementation of the ODH of ethane technology. Keeping this in mind, most of the research reported in the literature has been focused on different aspects of ODH catalysts, such as catalyst active phases, structure or morphology which are responsible for catalyst performance.

Like other conventional heterogeneous catalytic reactions, both the support and the active metal components play important roles in ODH reactions. The most commonly studied metals are V and Cr, using different types of support materials [M. Loukah, J. C. Vedrine, and M. Ziyad, "Oxidative dehydrogenation of ethane on V- and Cr-based phosphate catalysts," vol. 4, 1995—incorporated herein by reference in its entirety]. For example, the phosphate-supported V catalysts are more active and provide better ethylene selectivity than those which are reported for $(VO)_2 P_2O_7$ [P. Ciambelli, P. Galli, L. Lisi, M. A. Massucci, P. Patrono, R. Pirone, G. Ruoppolo, and G. Russo, "$TiO_2$ supported vanadyl phosphate as catalyst for oxidative dehydrogenation of ethane to ethylene," vol. 203, pp. 133-142, 2000—incorporated herein by reference in its entirety]. For a Cr-containing catalyst, it was shown that at comparable conversion levels, the ethylene selectivity varied according to different supports used: $(VO)_2P_2O_7 > CrPO_4 > Cr/\alpha\text{-}ZrP > Cr/\beta\text{-}ZrP$. Iron phosphate phases such as $FePO_4$, $Fe_2P_2O_7$, $\alpha\text{-}Fe_3(P_2O_7)$ and $\beta\text{-}Fe_3(P_2O_7)$, and non-stoichiometric (mixed) iron phosphate phases with P:Fe ratios of 1.2:1 and 2:1 have been also reported to be active for ODH reactions [J. E. Miller, M. M. Gonzales, L. Evans, A. G. Sault, C. Zhang, R. Rao, G. Whitwell, A. Maiti, and D. King-Smith, "Oxidative dehydrogenation of ethane over iron phosphate catalysts," Appl. Catal. A Gen., vol. 231, no. 1-2, pp. 281-292, May 2002—incorporated herein by reference in its entirety]. The nickel based Ni—Co/$Al_2O_3$ catalysts however, are shown to be active but to display low ethylene selectivity (less than 30%) [J. P. Bortolozzi, L. B. Gutierrez, and M. a. Ulla, "Synthesis of Ni/$Al_2O_3$ and Ni—Co/$Al_2O_3$ coatings onto AISI 314 foams and their catalytic application for the oxidative dehydrogenation of ethane," Appl. Catal. A Gen., vol. 452, pp. 179-188, February 2013—incorporated herein by reference in its entirety].

Several studies investigated different acidic SAPO-34 based support materials such as AlPO-34, SAPO-34, NaAPSO-34 and LaAPSO-34 in ODH catalysts. It was demonstrated that the cracking reactions were inhibited with the use of SAPO-34 catalysts. Thus, deactivation effects were practically absent, even during long times-on-stream in a laboratory scale reactor. Upon the introduction of active metals such as V, Co, Mg and Mn, the ALPO-5 supported catalysts showed improved activity. However, ethylene selectivity did not exceed 65% [L. Marchese, "Acid SAPO-34 Catalysts for Oxidative Dehydrogenation of Ethane," J. Catal., vol. 208, no. 2, pp. 479-484, June 2002—incorporated herein by reference in its entirety]. There are some studies that dealt with the acidic and basic Y zeolites supported transition metal (Ni, Cu, and Fe) catalysts in ODH reactions [X. Lin, C. a. Hoel, W. M. H. Sachtler, K. R. Poeppelmeier, and E. Weitz, "Oxidative dehydrogenation (ODH) of ethane with $O_2$ as oxidant on selected transition metal-loaded zeolites," J. Catal., vol. 265, no. 1, pp. 54-62, July 2009—incorporated herein by reference in its entirety]. Among these catalysts, the nickel-based catalysts show better activity and selectivity. Based on the catalyst activity and ethylene selectivity on these metal-loaded Y zeolites, samples were ranked as Ni/Y-zeolite>Cu/Y-zeolite>Fe/Y-zeolite [Y. Schuurman, V. Ducarme, T. Chen, W. Li, C. Mirodatos, and G. A. Martin, "Low temperature oxidative dehydrogenation of ethane over catalysts based on group VIII metals," Appl. Catal. A Gen., vol. 163, no. 1-2, pp. 227-235, December 1997—incorporated herein by reference in its entirety]. In order to improve the activity and selectivity of these catalysts Li, Mg, Al, Ga, Ti, Nb and Ta have been used as promoters [Y. Wu, J. Gao, Y. He, and T. Wu, "Preparation and characterization of Ni—Zr—O nanoparticles and its catalytic behavior for ethane oxidative dehydrogenation," Appl. Surf. Sci., vol. 258, no. 11, pp. 4922-4928, March 2012; H. Zhu, S. Ould-Chikh, D. H. Anjum, M. Sun, G. Biausque, J.-M. Basset, and V. Caps, "Nb effect in the nickel oxide-catalyzed low-temperature oxidative dehydrogenation of ethane," J. Catal., vol. 285, no. 1, pp. 292-303, January 2012—each incorporated herein by reference in its entirety].

Haddad and colleagues examined Mo-based catalysts having both V and phosphorous as promoters. These bimetallic catalysts were found to be effective, especially when both V and phosphorous were added together [N. Haddad, E. Bordes-Richard, L. Hilaire, and a. Barama, "Oxidative dehydrogenation of ethane to ethene on alumina-supported molybdenum-based catalysts modified by vanadium and phosphorus," Catal. Today, vol. 126, no. 1-2, pp. 256-263, August 2007—incorporated herein by reference in its entirety]. Vanadium with Ti, Sn or Zr pyrophosphates supports were studied in an ODH reaction [L. Lisi, G. Ruoppolo, M. P. Casaletto, P. Galli, M. a. Massucci, P. Patrono, and F. Pinzari, "Vanadium-metal(IV)phosphates as catalysts for the oxidative dehydrogenation of ethane," J. Mol. Catal. A Chem., vol. 232, no. 1-2, pp. 127-134, May 2005—incorporated herein by reference in its entirety]. Here, the catalyst exhibited a good conversion with selectivity up to 90%.

Cr-containing oxide pillared zirconium phosphate materials were synthesized using the fluoro-complex method which enhanced catalyst activity [B. Solsona, J. M. López-Nieto, M. Alcántara-Rodríguez, E. Rodríguez-Castellón, and a. Jiménez-López, "Oxidative dehydrogenation of ethane on Cr, mixed Al/Cr and mixed Ga/Cr oxide pillared zirconium phosphate materials," J. Mol. Catal. A Chem., vol. 153, no. 1-2, pp. 199-207, March 2000—incorporated herein by reference in its entirety]. A multicomponent $BaCl_2$—$TiO_2$—$SnO_2$ showed high selectivity of ethylene and low $CO_x$ selectivity [Z. Wang, L. Chen, G. Zou, X. Luo, R. Gao, L. Chou, and X. Wang, "A novel $BaCl_2$—$TiO_2$—$SnO_2$ catalyst for the oxidative dehydrogenation of ethane," Catal. Commun., vol. 25, no. 3, pp. 45-49, August 2012—incorporated herein by reference in its entirety]. It was believed that the presence of $Cl^-$ ions in the catalyst played vital and positive roles in the ODH reaction. Although this catalyst displayed promising results (e.g. 92.6% ethylene selectivity), the observed deactivation rate was very high. The catalyst activity sharply declined during the initial time on stream.

Other types of metals have been tested for ODH including La, Nd, Sm and Gd. The synthesis of these catalysts was effected using a modified sol-gel method [Q. Zhou, D. Zhou, Y. Wu, and T. Wu, "Oxidative dehydrogenation of ethane over RE-NiO (RE=La, Nd, Sm, Gd) catalysts," J. Rare Earths, vol. 31, no. 7, pp. 669-673, July 2013—incorporated herein by reference in its entirety]. Among these catalysts Gd—NiO displayed the best catalytic performance for the ODH reaction with 56% ethane conversion and 51% ethylene selectivity at 375° C. Cobalt-titanium (anatase) catalysts were also investigated alone and with addition of phosphorous [Y. Brik, "Titania-Supported Cobalt and Cobalt-Phosphorus Catalysts: Characterization and Performances in Ethane Oxidative Dehydrogenation," J. Catal., vol. 202, no. 1, pp. 118-128, August 2001—incorporated herein by reference in its entirety]. It was shown in this respect that the addition of vanadium and phosphorous can enhance the ethane conversion, the ethylene selectivity and the catalyst stability and selectivity. This is the case despite the fact that Mo is more effective in the same aspects [N. Haddad, E. Bordes-Richard, and a. Barama, "$MoO_x$-based catalysts for the oxidative dehydrogenation (ODH) of ethane to ethylene," Catal. Today, vol. 142, no. 3-4, pp. 215-219, April 2009—incorporated herein by reference in its entirety].

Regarding mixed oxides, NiO—$CeO_2$ has also been investigated. It has been shown that the addition of cerium oxide to NiO improves ODH catalyst performance [B. Solsona, J. M. López-Nieto, M. Alcántara-Rodríguez, E. Rodríguez-Castellón, and a. Jiménez-López, "Oxidative dehydrogenation of ethane on Cr, mixed Al/Cr and mixed Ga/Cr oxide pillared zirconium phosphate materials," J. Mol. Catal. A Chem., vol. 153, no. 1-2, pp. 199-207, March 2000—incorporated herein by reference in its entirety]. $V_2O_5/Nb_2O_5$ catalysts with various $V_2O_5$ contents were also studied [A. Qiao, V. N. Kalevaru, J. Radnik, a. Srihari Kumar, N. Lingaiah, P. S. Sai Prasad, and a. Martin, "Oxidative dehydrogenation of ethane to ethylene over V2O5/Nb2O5 catalysts," Catal. Commun., vol. 30, pp. 45-50, January 2013—incorporated herein by reference in its entirety]. This showed a 38% selectivity and 28% ethylene yield although pure $Nb_2O_5$ had very little activity by itself.

All of the above described studies were conducted in fixed reactors using air as an oxidizing source. This contributed to the $CO_x$ formation due to complete oxidation of both the ethane fed and the ethylene product. Consequently, the ethylene selectivity was consistently low. Other drawbacks of the fixed bed ODH include catalyst deactivation as a result of coke formation, difficulty in separation of ODH products from the $CO_x$ and accumulation of residual nitrogen when using air directly as the oxygen carrier.

It has been shown that combustion reactions can considerably be reduced by controlling the availability of gas phase oxygen. One of the possible alternatives is a gas phase, oxygen-free ODH in a circulating fluidized bed reactor, [S. Al-Ghamdi, M. Volpe, M. M. Hossain, and H. de Lasa, "$VO_x/c$-$Al_2O_3$ catalyst for oxidative dehydrogenation of ethane to ethylene: Desorption kinetics and catalytic activity," Appl. Catal. A Gen., vol. 450, pp. 120-130, January 2013; Bakare, I. A., Shamseldin M., Razzak, S. A., Al-Ghamdi, S., Hossain, M. M., de Lasa, H. I., Fluidized bed ODH of ethane to ethylene over $VOx$-$MoO_x/\gamma$-$Al_2O_3$ catalyst: Desorption kinetics and catalytic activity, Chemical Engineering Journal, doi:10.1016/j.cej.2014.09.11—each incorporated herein by reference in its entirety]. Using this approach, the lattice oxygen is the one available for ODH. Once the catalyst is lattice oxygen depleted it can be transported and re-oxidized in a catalyst regenerator with a continuous air flow at a suitable temperature. It has been shown that up to 84.5% ethylene selectivity can be obtained in the temperature range of 550-600° C. Furthermore, the selectivity of the $VO_x$ based catalyst can be further improved with a $MoO_x$ modifications [Bakare, I. A., Shamseldin M., Razzak, S. A., Al-Ghamdi, S., Hossain, M. M., de Lasa, H. I., Fluidized bed ODH of ethane to ethylene over $VOx$-$MoO_x/\gamma$-$Al_2O_3$ catalyst: Desorption kinetics and catalytic activity, Chemical Engineering Journal, doi:10.1016/j.cej.2014.09.11—incorporated herein by reference in its entirety]. It has been shown that $MoO_x$ enhances the reducibility of the $VO_x$ by preventing the formation of crystalline $VO_x$ phase and as a result ethane conversion is increased. Despite these valuable prospects, both the $VO_x$ and the $VO_x$—$MoO_x$ catalysts show decreased ethylene selectivity above ~600° C. The high reaction temperature favors complete oxidation of ethane/ethylene to $CO_x$ in these catalysts.

Thus the selection of reaction temperature continues to be an issue in ODH. On one hand, one would like to operate the ODH reactor at the highest possible thermal level to achieve high ODH reaction rates. Reactor designers are striving to minimize reactor volumes by enhancing reaction rate. However, and from a practical view point, temperatures above 675° C. may favor thermal cracking of ethane (gas phase). Thus, one has to limit the ODH reaction temperature to 600° C. using a catalyst which display an appreciable reaction rate and give high ethylene selectivity [Bakare, I. A., Shamseldin M., Razzak, S. A., Al-Ghamdi, S., Hossain, M. M., de Lasa, H. I., Fluidized bed ODH of ethane to ethylene over $VOx$-$MoO_x/\gamma$-$Al_2O_3$ catalyst: Desorption kinetics and catalytic activity, Chemical Engineering Journal, doi:10.1016/ j.cej.2014.09.11—incorporated herein by reference in its entirety]. In addition, and if one consider the integrated ODH process having an ODH fluidized bed reactor and a fluidized catalyst regenerator, it appears the 600° C. thermal level provides a good compromise, eliminating the need of cooling and heating exchangers between the interconnected twin fluidized beds.

In light of the foregoing there remains an unmet need for solutions, such as catalysts, reactor design and reaction conditions, that effectively overcome the drawbacks of oxidative dehydrogenation reactions and improve their reactivity.

BRIEF SUMMARY OF THE INVENTION

In a first aspect, the present disclosure relates to a fluidizable catalyst for oxidative dehydrogenation of an alkane. The catalyst comprises a zirconia-modified alumina support material and 10-20% of one or more vanadium oxides by weight based on the total catalyst weight, the one or more vanadium oxides being adsorbed onto the support material. The support material comprises an alumina/zirconia weight ratio of 1-5:1-3.

In certain embodiments, the one or more vanadium oxides are selected from the group consisting of $V_2O_5$, $VO_2$ and $V_2O_3$.

In some embodiments, the fluidizable comprises at least 50% of $V_2O_5$ based on total weight of the one or more vanadium oxides.

In some embodiments, the alumina/zirconia weight ratio is 1-2:1.

In some embodiments, the one or more vanadium oxides form a crystalline phase on the surface of the zirconia-modified alumina support material.

In one or more embodiments, the fluidizable catalyst has an average particle size of 40-120 μm.

In one or more embodiments, the fluidizable catalyst comprises a plurality of particles and more than 75% of the particles being in the 40-120 μm.

In one or more embodiments, the fluidizable catalyst has an apparent particle density of 1.5-3.5 g/cm$^3$.

In at least one embodiment, the fluidizable catalyst has Class B powder properties in accordance with Geldart particle classification.

In certain embodiments, the fluidizable catalyst has a BET surface area of 10-50 m$^2$/g.

In one or more embodiments, the zirconia present in the alumina/zirconia ratio depresses the surface acidity of the catalyst.

In one or more embodiments, the zirconia present in the alumina/zirconia ratio enhances the interaction between the one or more vanadium oxides and the support material.

In one or more embodiments, the zirconia present in the alumina/zirconia ratio enhances the reducibility of the one or more vanadium oxides.

In a second aspect, the present disclosure provides a process for converting an alkane to a corresponding olefin. The process comprises contacting an alkane feed stream with the fluidizable catalyst of the first aspect of the invention in an oxygen-free atmosphere at 525-675° C.

In certain embodiments, the alkane is selected from the group consisting of ethane, propane, n-butane and isobutane.

In some embodiments, the catalyst is present at an amount of 0.05-0.5 g/ml per ml of the alkane feed stream.

In one embodiment, the alkane is ethane and the process has an ethane conversion of 15-45%.

In one embodiment, the alkane is ethane and the process has an ethylene selectivity of 75-90%.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
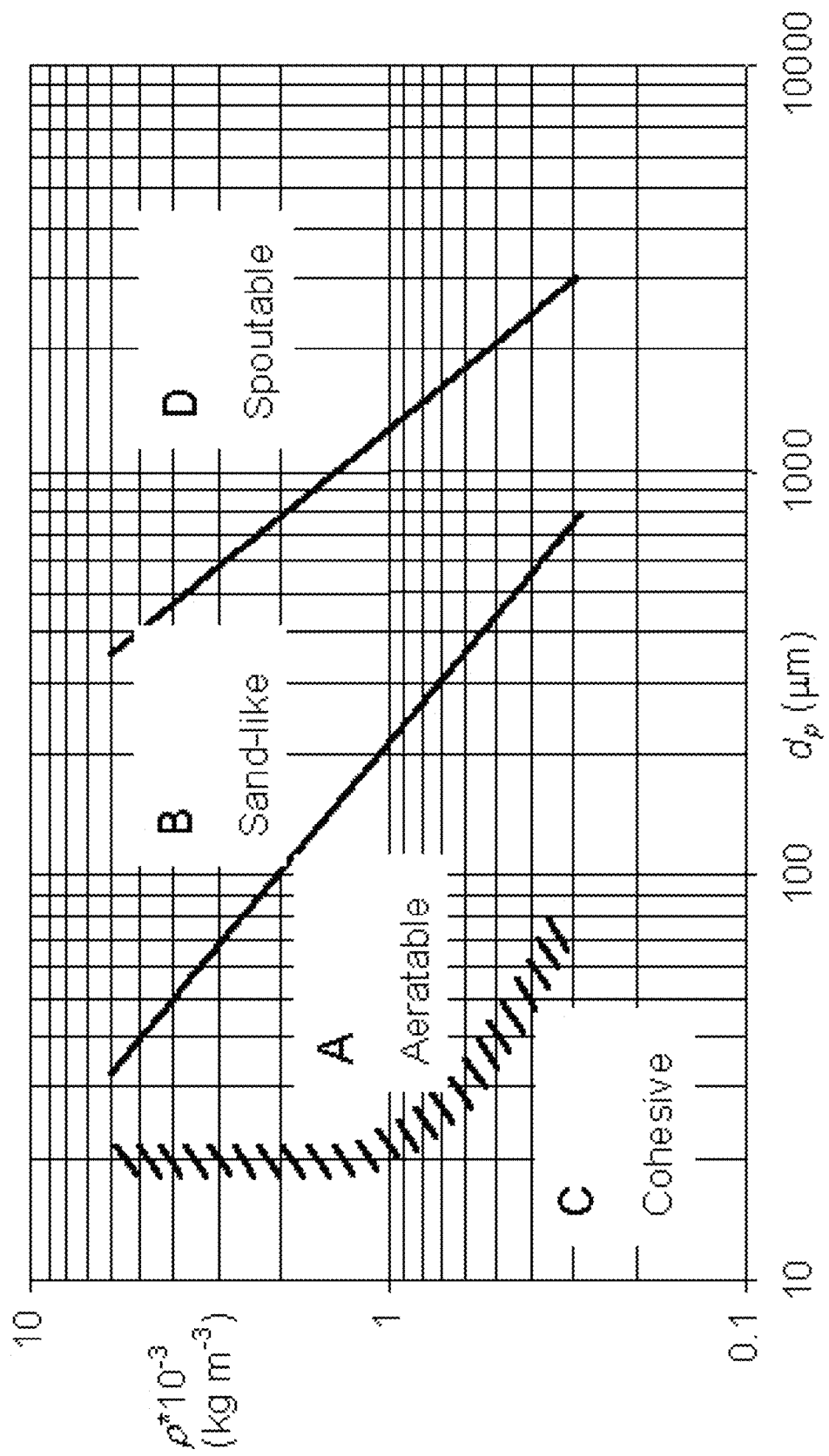
FIG. 1 is the Geldart diagram for classification of particle fluidization.

Referring now to the drawings, wherein like reference numerals designate identical or corresponding parts throughout the several views.

In the present disclosure, there are provided catalysts for oxidative dehydrogenation (ODH) of alkanes in reactors having a fluidized bed design. These catalysts contain one or more oxides of vanadium ($VO_x$) as catalytic material, which are adsorbed and mounted upon zirconia or $ZrO_2$-modified alumina support material.

In a fluidized bed reactor, before the reactor is started, the catalyst pellets lie on a grate at the bottom of the reactor. Reactants are continuously pumped into the reactor through a distributor causing the bed to become fluidized. During the fluidization, the catalyst pellets are converted from a static solid-like state to a dynamic fluid-like state. The bed's behavior after initial fluidization depends on the state of the reactant. If it is a liquid the bed expands uniformly with increased upward flow of the reactant, resulting in a homogenous fluidization. If the reactant is a gas, the bed will be non-uniform because the gas forms bubbles in the bed, resulting in aggregative fluidization. In the present disclosure, the reactant or feed is a light alkane such as but not limited to ethane, propane and butane (including n-butane and isobutane), all of which are gases and hence, an aggregative fluidization may be more probable.

Properties or parameters for determining the fluidizability of a catalyst include but are not limited to average particle size, and particle size distribution. The average particle size and the particle size distribution can be measured, for example, using a Mastersizer 2000 from Malvern Instruments. The apparent particle density can be assessed using a CREC-established method. In the method, a known amount of catalyst is introduced to a flask. The flask is filled with isopropanol and the apparent particle density, AD, is calculated using the following equation:

$$AD = \frac{W_{cat}}{V_T - V_{isopropanol}} \quad \text{(Eq. 1)}$$

where AD is the apparent particle density (g/cm$^3$) $W_{cat}$ is the catalyst weight, $V_r$ is the flask volume and $V_{isopropanol}$ is the volume of isopropanol calculated as the ratio of the weight of isopropanol needed to fill the flask and the density of isopropanol.

A catalyst in accordance with the present disclosure has an average particle size (diameter) of 40-120 μm, preferably 50-100 μm, more preferably 60-80 μm. The particle size distribution is 20-180 μm where more than 75% of the particles are 40-120 μm, preferably more than 80%, more preferably more than 85%, even more preferably more than 90%. The apparent particle density of the catalyst is 1.0-4.0 g/cm$^3$, preferably 1.5-3.5 g/cm$^3$, more preferably 1.8-3.2 g/cm$^3$.

In some embodiments, with the calculated average particle size and particle apparent density values, the fluidization regime of the vanadia-zirconia-alumina catalyst particles of the present disclosure can be determined using Geldart's powder classification chart of FIG. 1 [Geldart, D. (1973). "Types of Gas Fluidization." *Powder Technology*, 7, 285-292—incorporated herein by reference in its entirety]. In at least one embodiment, the catalyst particles display a Geldart Class B powder property, which is highly fluidizable under ODH conditions. Large particles, such as those under Geldart Class D, may limit the gas phase reactant access to the inner layers of the catalyst. As a result, using smaller particles can minimize the diffusional resistance and reduction/oxidation rates can be maximized. On the other hand, very small particles, such as those under Geldart's Class C, can cause fluidization problems, channeling and loss of fines. In addition, these very fine particles fluidize under very difficult to attain conditions, and may require the application of an external force, such as mechanical agitation.

In certain embodiments, the fluidizability of the catalysts is demonstrated in a Plexiglas unit with dimensions matching the one of a CREC riser simulator.

Accordingly, the fluidizable catalysts of the present disclosure contain 10-20% of one or more vanadium oxides as catalytic material by weight based on the total catalyst weight, preferably 12-18%, more preferably 12.5-17.5%. The vanadium oxides are of formula $V_xO_y$, wherein x=1-2 and y=2-5, preferably selected from the group consisting of $V_2O_5$, $VO_2$ and $V_2O_3$. In certain embodiments, the catalysts are substantially free of $V_2O_3$, and contain a mixture of at least 50% $V_2O_5$ based on total weight of vanadium oxides, with the rest being $VO_2$, preferably 75-80% $V_2O_5$, more preferably 85-90% $V_2O_5$, even more preferably at least 90-95% $V_2O_5$, most preferably 95-99.9% $V_2O_5$. In some embodiments, the catalysts consist essentially of $V_2O_5$ and are substantially free of $V_2O_3$ and $VO_2$.

The vanadium oxide catalytic material is loaded on a zirconia-alumina inert support. The zirconia-alumina support comprises zirconia ($ZrO_2$) and alumina ($Al_2O_3$) at different alumina/zirconia weight ratios: 5:3, 5:2, 5:1, 4:3, 4:1, 3:2, 3:1, 2:1, 1:1 or 1:2, preferably 4:1, 3:2, 3:1, 2:1 or 1:1, more preferably 2:1 or 1:1 or any range, fractional or whole, between the aforementioned ranges. In one embodiment, the alumina/zirconia weight ratio in the support material is 2:1. The alumina-based support material may be comprised of a plurality of different crystallographic phases. Examples of alumina-based inert material include but are not limited to aluminum oxide, alumina, alumina monohydrate, alumina trihydrate, alumina-silica, bauxite, calcined aluminum hydroxides such as gibbsite, bayerite and boehmite, α-alumina, transition aluminas such as γ-alumina, η-alumina and δ-alumina, and calcined hydrotalcite. In at least one embodiment, the support material is γ-alumina-based (γ-$Al_2O_3$).

To modify the alumina support with zirconia ($ZrO_2$), an alumina support can be initially calcined to remove moisture and other volatile compounds then immersed in a solution containing a zirconium precursor salt (e.g. zirconium tetrachloride) and an organic solvent such as toluene, for 12-24 h and preferably with stirring to achieve a homogeneous mixture. The soaked alumina support can then be dried by calcination again. In general, the zirconia modification is found to have the effect of reducing the BET (Brunauer-Emmett-Teller) surface area of the alumina. The zirconia-modified alumina support has a BET surface area of 10-50 m$^2$/g, preferably 15-40 m$^2$/g, more preferably 20-30 m$^2$/g.

To deposit and adsorb the catalytic material onto the zirconia-modified alumina support, a similar soaking impregnation method as described above may be used, with a vanadium(IV) or a vanadium(V) precursor salt such as vanadyl acetylacetonate, vanadyl sulfate, vanadium pentoxide, vanadium oxytripropoxide, tetrakis(diethylamido)vanadium. The vanadium precursor is preferably phosphorus-free. It is during the post-soaking calcination that the vanadium salt is converted into one or more vanadium oxides.

In addition to the effect on surface area, the zirconia modification also depresses the surface acidity and metal-support interaction of the catalyst, thereby enhancing olefin selectivity in ODH reactions and reducing coke ($CO_x$) formation. Catalyst acidity plays a major role in metal support interaction affecting $VO_x$ reducibility. Reducibility may control catalyst activity and selectivity by providing $O_2$ for oxidation, with high acidity not favoring able selective oxidation.

The effects of the zirconia modification can be established by at least $NH_3$ desorption kinetics analysis, and the vanadia-zirconia-alumina catalysts provided herein have an estimated energy of $NH_3$ desorption of 70-90 kJ/g, preferably 72-85 kJ/g, more preferably 75-82 kJ/g. Furthermore, as evaluated by X-ray diffraction, the vanadia catalytic material (comprising one or more vanadium oxides as described herein) forms a crystalline phase on the zirconia-alumina support surface. In the absence of the zirconia modification of the alumina support, the catalyst would display an amorphous phase.

The present disclosure also relates to a process of converting an alkane to a corresponding olefin by oxidative dehydrogenation in the presence of a fluidizable catalyst described herein.

Alkane oxidative dehydrogenation (ODH) reactions incorporating a vanadia-zirconia-alumina fluidizable catalyst provided herein are preferably operated in an oxygen-free environment or atmosphere at temperatures ranging 525-675° C., preferably 550-625° C., more preferably 575-600° C., at standard pressure (100 kPa/1 bar/14.5 psi 0.9869 atm) and a minimum catalyst-alkane feed contact time of 15 s to 1 min, preferably 20-50 s, more preferably 30-45 s. The amount of catalyst present in an ODH reaction is 0.05-0.5 g/ml per ml of alkane feed injected, preferably 0.1-0.4 g/ml, more preferably 0.15-0.3 g/ml. Under these operating conditions, an alkane is converted to a corresponding olefin in accordance with the equation below:

$$C_yH_{2y+2} + \tfrac{1}{2}V_2O_5 \rightarrow C_yH_{2y} + H_2O + \tfrac{1}{2}V_2O_3 \quad \text{(Eq. 2)}$$

where y is 2, 3 or 4.

In some embodiments, the alkane-olefin conversion may be accompanied by the following complete oxidation of the alkane or the olefin as side, secondary reactions:

$$C_yH_{2y+2} + \tfrac{1}{2}V_2O_5 \rightarrow aCO_2 + bCO + (2y-2)/2 H_2O + \tfrac{1}{2}V_2O_3 \quad \text{(Eq. 3)}$$

$$C_yH_{2y} + \tfrac{1}{2}V_2O_5 \rightarrow aCO_2 + bCO + 2y/2 H_2O + \tfrac{1}{2}V_2O_3 \quad \text{(Eq. 4)}$$

where y is 2, 3 or 4 and y=a+b

With the use of the vanadia-zirconia-alumina fluidizable catalyst, an ODH reaction has an alkane conversion rate, as defined with the equation below, of up to 50%, preferably 15-45%, more preferably 17-40%. In at least one embodiment, the alkane converted is ethane and the corresponding olefin is ethylene.

$$\text{Conversion of alkane} = \frac{\text{Moles of alkane converted}}{\text{Moles of alkane fed}} \times 100\% \quad \text{(Eq. 5)}$$

The selectivity to the corresponding olefin or $CO_x$ is calculated as:

$$\text{Selectivity to product} = \frac{\text{Moles of product}}{\text{Moles of alkane reacted} - \text{Moles of product}} \times 100\% \quad \text{(Eq. 6)}$$

The olefin selectivity is at least 75%, preferably 80-90%, more preferably 85-90%.

EXAMPLES

In the following examples, the effects of $ZrO_2$ modification on the fluidizable $VO_x/\gamma$-$Al_2O_3$—$ZrO_2$ catalysts for oxidative dehydrogenation (ODH) of ethane to ethylene were investigated. These examples are provided to further illustrate the numerous embodiments of the present disclosure, and are not intended to limit the scope of the appended claims. The synthesized catalysts were characterized using different physiochemical techniques. The gas phase, oxygen-free ODH (of ethane) experiments were established in a CREC-Riser Simulator under various reaction conditions. The main findings of these examples are provided in the following paragraphs:

From the XRD analysis, it is shown that both $V_2O_5$ and $ZrO_2$ species are present on the $VO_x/\gamma$-$Al_2O_3$—$ZrO_2$ catalysts. XRD patterns also demonstrate that $VO_x$ is present in the prepared catalyst in a crystalline phase, with the formation of this crystalline phase being promoted by the $ZrO_2$. Samples of $VO_x/\gamma$-$Al_2O_3$ catalyst display an amorphous phase only.

From the temperature-programmed reduction (TPR) experiments, it is demonstrated that good $V_2O_5$ reduction activity occurs at low $ZrO_2$ content (2:1 ratios). TPR/TPO oxidation-reduction cycles show good catalyst stability. Increasing $ZrO_2$ content decreases the percent of metal reduction.

$NH_3$-TPD measurements confirm the existence of weak acid sites on the $VO_x/\gamma$-$Al_2O_3$—$ZrO_2$. The desorption kinetics suggests a medium range of interaction energies involved between $VO_x$ and the support, with this likely enhancing metal reducibility.

ODH of ethane in the presence of $VO_x/\gamma$-$Al_2O_3$—$ZrO_2$ and under free oxygen atmosphere shows that ethylene, CO and $CO_2$ are the major products.

Among the three samples prepared, the catalyst with $\gamma$-$Al_2O_3$:$ZrO_2$=2:1 ratio gives the highest ethane conversion (37.9%). This result is in agreement with TPR analysis which shows best reducibility (highest $H_2$ consumption) for this catalyst.

The $VO_x/\gamma$-$Al_2O_3$—$ZrO_2$ fluidizable catalyst ($\gamma$-$Al_2O_3$:$ZrO_2$=2:1) displays ethylene selectivity up to 90% (at 600° C.) while the unmodified $VO_x/\gamma$-$Al_2O_3$ catalyst gives 42% ethylene selectivity under same reaction conditions.

$ZrO_2$ addition alters the acidity and structure of the alumina support which influences the formation of $VO_x$ (mono or poly). The $ZrO_2$ also affects the metal support interaction and plays a critical role in lowering $VO_x$ reducibility, therefore allowing an increased ethylene selectivity due to a promoted oxygen controlled release rate.

Example 1

Catalyst Preparation

Impregnation by a soaking (excess of solvent) technique was used to prepare catalyst samples [M. A. Bañares, M. V Mart, X. Gao, J. L. G. Fierro, and I. E. Wachs, "Dynamic behavior of supported vanadia catalysts in the selective oxidation of ethane In situ Raman, UV-Vis DRS and reactivity studies," vol. 61, pp. 295-301, 2000—incorporated herein by reference in its entirety]. Before metal loading, the alumina support was calcined under pure $N_2$ flow at 500° C. for 4 h, to remove moisture and volatile compounds. The calcined sample was placed in a beaker and toluene was added. Zirconium tetrachloride was then added to the beaker, and the mixture was left under stirring for 12 h. The sample was filtered from the solvent and dried at ambient conditions. After complete drying, the sample was calcined again at 500° C. for 5 h to remove the solvent. Three support samples were prepared with γ-$Al_2O_3$/$ZrO_2$ weight ratios of 2:1, 1:1 and 1:2.

Accordingly, three catalyst samples were prepared by dispersing 15 wt % of V on each of the above γ-$Al_2O_3$—$ZrO_2$ supports. Vanadyl acetylacetonate (Aldrich, 97%) was used as precursor for vanadium loading. The V loading was also accomplished using the same approach as $ZrO_2$ loading. The $ZrO_2$-modified $Al_2O_3$ support and vanadyl acetylacetonate, were added to a beaker containing toluene. The mixture was stirred for 24 h, to obtain a homogeneous mixture which facilitated better metal dispersion. The solid sample was separated by vacuum filtration and dried at ambient temperature. The dried sample was then reduced with hydrogen (10% $H_2$ and 90% Ar) at 500° C. in a fluidized bed reactor. Finally, the reduced sample was calcined under air at 500° C. for 4 h to obtain the oxide for of the catalyst. After this treatment, catalyst color became yellow indicating the presence of $V_2O_5$ on the support surface.

Example 2

Elemental and BET Surface Area Analyses of Catalysts

XRF analysis was used to determine elements and compound ratios in each sample after synthesis. A Bruker Tornado M4 Micro-XRF Analyzer, equipped with a single High Performance XFlash Detector and a 25 μm diameter spot size, was employed for XRF analysis.

The nitrogen adsorption and BET surface area of the $VO_x$/$Al_2O_3$—$ZrO_2$ catalyst samples were determined in a Quantachrome ASIQwin. The nitrogen adsorption was carried out at 77 K. For each experiment, 0.40-0.50 g of catalyst sample was degassed at 350° C. for 2 h. The adsorption isotherms were measured in the 0.04 to 1 kcal/mol relative pressure range.

Figure 2:
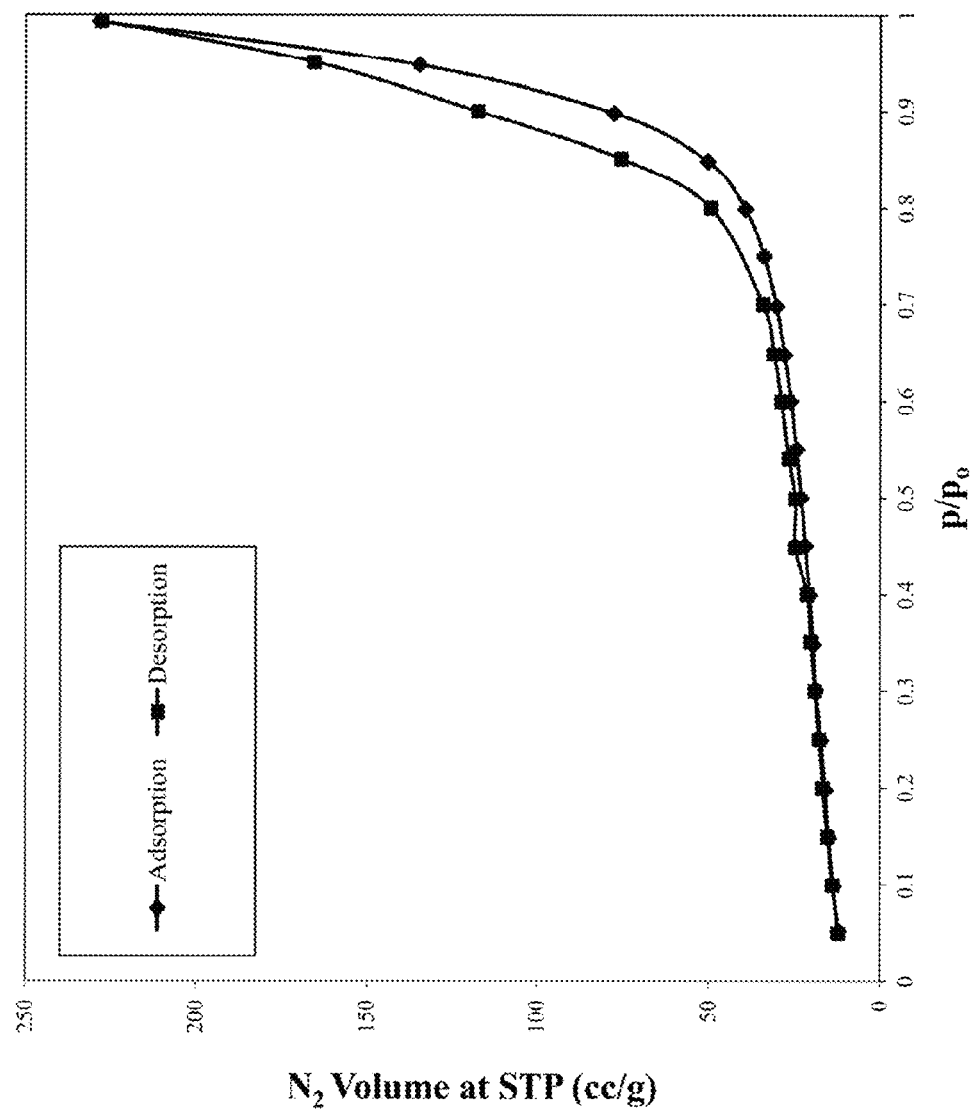
FIG. 2 is a curve showing N2 adsorption/desorption isotherms of 15% $VO_x$/Al2O3-$ZrO_2$ (2:1) catalyst sample.

The XRF results as shown in Table 1, indicate that compound percentages are equal to what was targeted, with a slight deviation. The nitrogen isotherm analysis was conducted to understand the adsorption/desorption characteristics of the catalyst sample. FIG. 2 shows the adsorption/desorption isotherms of a $ZrO_2$ modified $VO_x$/γ-$Al_2O_3$—$ZrO_2$ sample synthesized for this study. The sample shows a Type-V isotherm indicating narrow size mesoporosity [X. Lin, K. R. Poeppelmeier, and E. Weitz, "Oxidative dehydrogenation of ethane with oxygen catalyzed by K—Y zeolite supported first-row transition metals," Appl. Catal. A Gen., vol. 381, no. 1-2, pp. 114-120, June 2010—incorporated herein by reference in its entirety]. The isotherm data was further processed to determine the BET surface of the sample. The calculated BET surface area and the monolayer volume are also presented in Table 1. The BET surface area of the $ZrO_2$ modified sample is lower than the surface of the bare γ-$Al_2O_3$ support (141 $m^2$/g). The dispersed $ZrO_2$ and the vanadium species occupied the support pores, which contributed to the decrease of the surface area.

The monolayer volume of the adsorbed nitrogen can be calculated by Eq. 7:

$$n_m = \frac{S_{BET}}{A_m \times N}$$ (Eq. 7)

where, (1) $S_{BET}$ is the BET surface area $m^2$, (2) N represents Avogadro's constant and molecule/mol, (3) $A_m$ stands for the volume occupied by one $N_2$ gas molecule (0.162 $m^2$), and (4) $n_m$ denotes the monolayer volume per gram catalyst. The monolayer coverage occurs after 0.75 relative pressure indicates good dispersion of active sites and their availability for adsorption. This was expected as the catalyst was synthesized by soaking impregnation which provided good metal dispersion and thus, a satisfactory monolayer volume.

TABLE 1

XRF[a] and BET surface area characterization results.

| Sample | $VO_x$ % | $Al_2O_3$ % | $ZrO_2$ % | BET surface area ($m^2$/g · cat) | Monolayer volume ($cm^3$/g) |
| --- | --- | --- | --- | --- | --- |
| 15% $VO_x$/$Al_2O_3$—$ZrO_2$(2:1) | 14.4 | 57.2 | 28.4 | 24.1 | 2.4 × $10^{-4}$ |

[a]Catalyst elements percentages are within ±2% accuracy.

Example 3

X-Ray Diffraction Analysis of Catalysts

X-ray diffraction (XRD) analysis was conducted to identify the crystallographic structure of catalyst samples. XRD patterns of all catalysts reported in this study, were recorded on a Rigaku MiniFlex Diffractometer with monochromatic Cu Kα radiation (λ=0.15406 nm, 30 kV, 15 mA) using the normal scan rate of 4°/min. X-rays were collected using a 1.25° divergent scattering slit, and a 0.13 mm receiving slit. Samples were scanned within the 2θ range of 20-80° with a step size of 0.005°.

Figure 3:
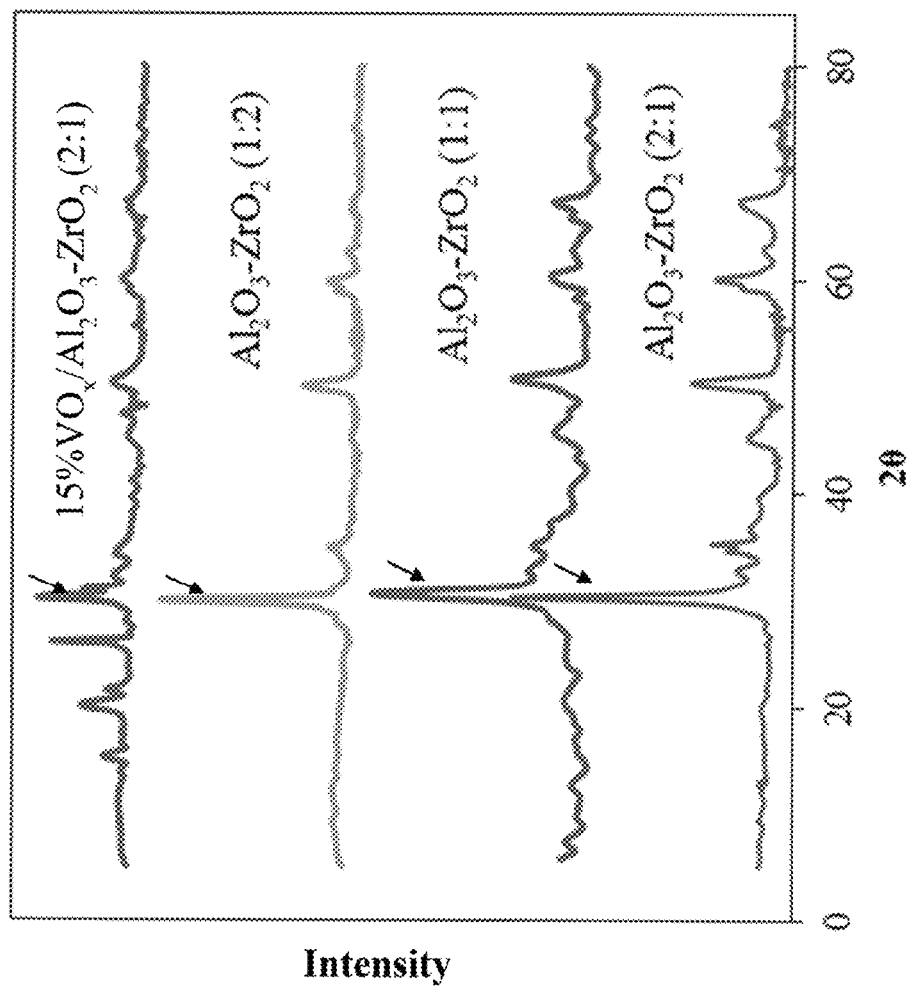
FIG. 3 shows the XRD patterns of various $Al_2O_3$—$ZrO_2$ catalysts, with the arrows indicating the peaks for $V_2O_5$.

FIG. 3 shows the XRD patterns of the various γ-$Al_2O_3$/$ZrO_2$ containing support samples and the $VO_x$/γ-$Al_2O_3$—$ZrO_2$ catalyst after $VO_x$ loading. The $V_2O_5$ was detected in the range of 2θ from 10 to 40° [F. Klose, T. Wolff, H. Lorenz, a Seidelmorgenstern, Y. Suchorski, M. Piorkowska, and H. Weiss, "Active species on γ-alumina-supported vanadia catalysts: Nature and reducibility," J. Catal., vol. 247, no. 2, pp. 176-193, April 2007—incorporated herein by reference in its entirety]. Peaks of t-$ZrO_2$ can also be found at 2θ of 30°, 48° and 65° while γ-$Al_2O_3$ peaks appeared at 2θ of 45° and 60°.

It can be seen in FIG. 3 that the $V_2O_5$ peak intensity was sharply decreased with decreasing the γ-$Al_2O_3$ to $ZrO_2$ ratios (increasing in $ZrO_2$ contents). Only $VO_2$ was obtained on the support surface in γ-$Al_2O_3$—$ZrO_2$ (1:2), which resulted in lower oxygen-carrying capacity and therefore lowers catalyst activity.

Furthermore, $ZrO_2$ introduced a crystal phase to the catalyst, in comparison with the catalyst sample without $ZrO_2$ [S. Al-Ghamdi, M. Volpe, M. M. Hossain, and H. de Lasa, "$VO_x$/c-$Al_2O_3$ catalyst for oxidative dehydrogenation of ethane to ethylene: Desorption kinetics and catalytic activity," Appl. Catal. A Gen., vol. 450, pp. 120-130, January 2013—incorporated herein by reference in its entirety]. This crystal phase is not detected by XRD and may reduce the oxygen-carrying capacity and the catalyst activity by increasing active site agglomeration.

Example 4

Temperature Programmed Reduction/Oxidation (TPR/TPO) Experiments

The TPR/TPO experiments were conducted using a Micromeritics AutoChemII 2920 Analyzer. The purpose of the TPR/TPO cycles was to determine catalyst reduction temperature, maximum temperature and catalyst stability during reduction-oxidation cycles. It is reported that during reduction/oxidation at high temperatures, vanadium dispersion changes [E. López, E. Heracleous, A. a. Lemonidou, and D. O. Borio, "Study of a multitubular fixed-bed reactor for ethylene production via ethane oxidative dehydrogenation," Chem. Eng. J., vol. 145, no. 2, pp. 308-315, December 2008—incorporated herein by reference in its entirety] when $VO_x$ phase interact on the support surface [M. Argyle, "Effect of Catalyst Structure on Oxidative Dehydrogenation of Ethane and Propane on Alumina-Supported Vanadia," J. Catal., vol. 208, no. 1, pp. 139-149, May 2002.—incorporated herein by reference in its entirety]. As a result, the catalyst activity and stability changes significantly [S. Al-Ghamdi, M. Volpe, M. M. Hossain, and H. de Lasa, "$VO_x$/c-$Al_2O_3$ catalyst for oxidative dehydrogenation of ethane to ethylene: Desorption kinetics and catalytic activity," Appl. Catal. A Gen., vol. 450, pp. 120-130, January 2013—incorporated herein by reference in its entirety].

At the beginning of each experiment, argon (99.9%) was introduced at rate of 50 ml/min while the temperature was increased to 300° C. for a period of 3 h. The system was cooled to ambient temperature and $H_2$/Ar gas mixture (10% $H_2$) was circulated at a rate of 50 ml/min. At after the gas flow reached to steady state, the catalyst bed temperature was raised to 750° C. at a heating rate of 10° C./min. The $H_2$ concentration of the gas leaving the catalyst bed was measured using a thermal conductivity detector (TCD). The detector signal was calibrated to a volume of $H_2$ consumed cc/g catalyst. A plot of the volume of $H_2$ consumption versus time/temperature represents the reduction profile of the catalyst sample. The area under the TPR profiles represents the total hydrogen consumption of the catalyst samples.

TPR/TPO characterization is an important technique for oxygen free ODH catalyst characterization. TPR simulates the ODH reaction as shown in Eq. 2 and Eq. 3: Reduction of the ODH catalyst during TPR with hydrogen:

$$V_2O_5 + 2H_2 \rightarrow V_2O_3 + 2H_2O \qquad (Eq. 8)$$

Reduction of the ODH catalyst with ethane:

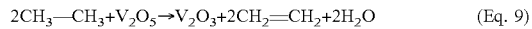

$$2CH_3-CH_3 + V_2O_5 \rightarrow V_2O_3 + 2CH_2=CH_2 + 2H_2O \qquad (Eq. 9)$$

Figure 4A:
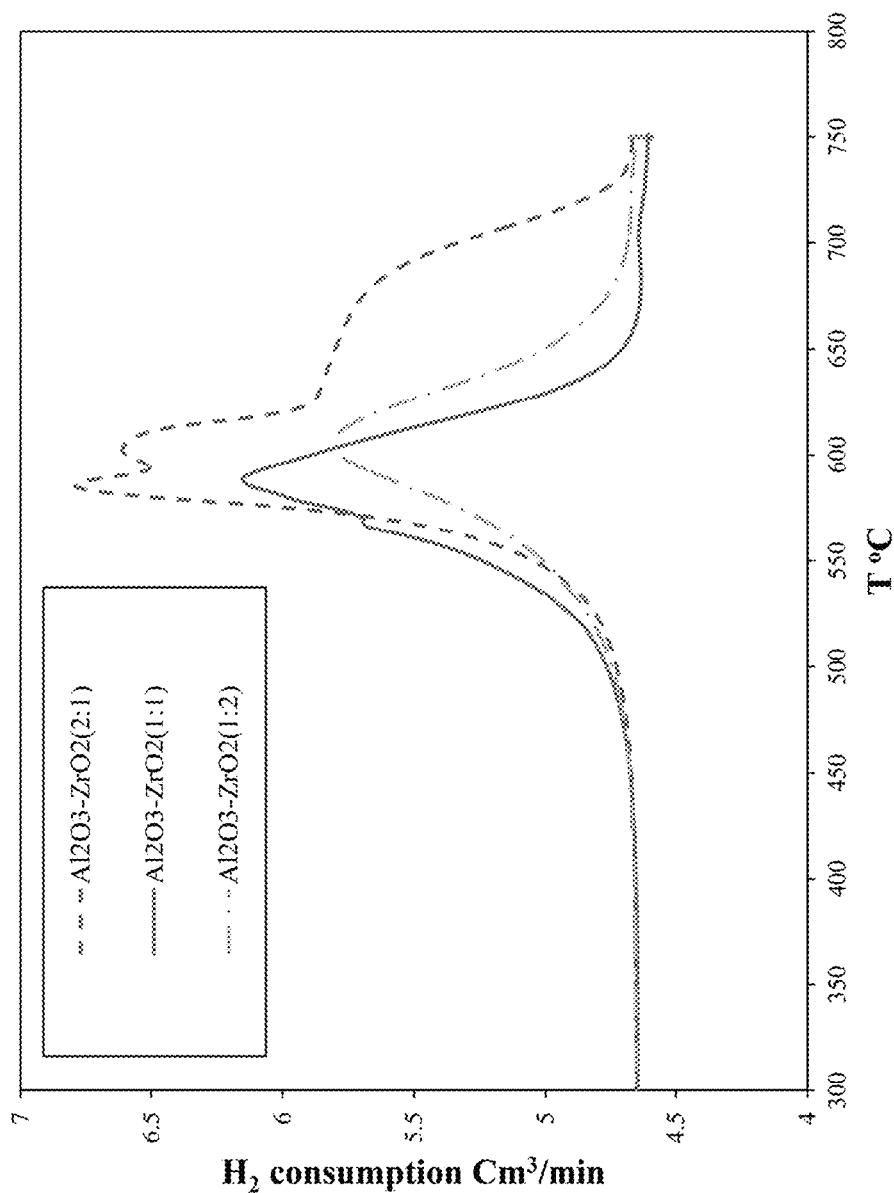
FIG. 4A shows the TPR profiles for various $Al_2O_3$—$ZrO_2$ catalysts.
Figure 4B:
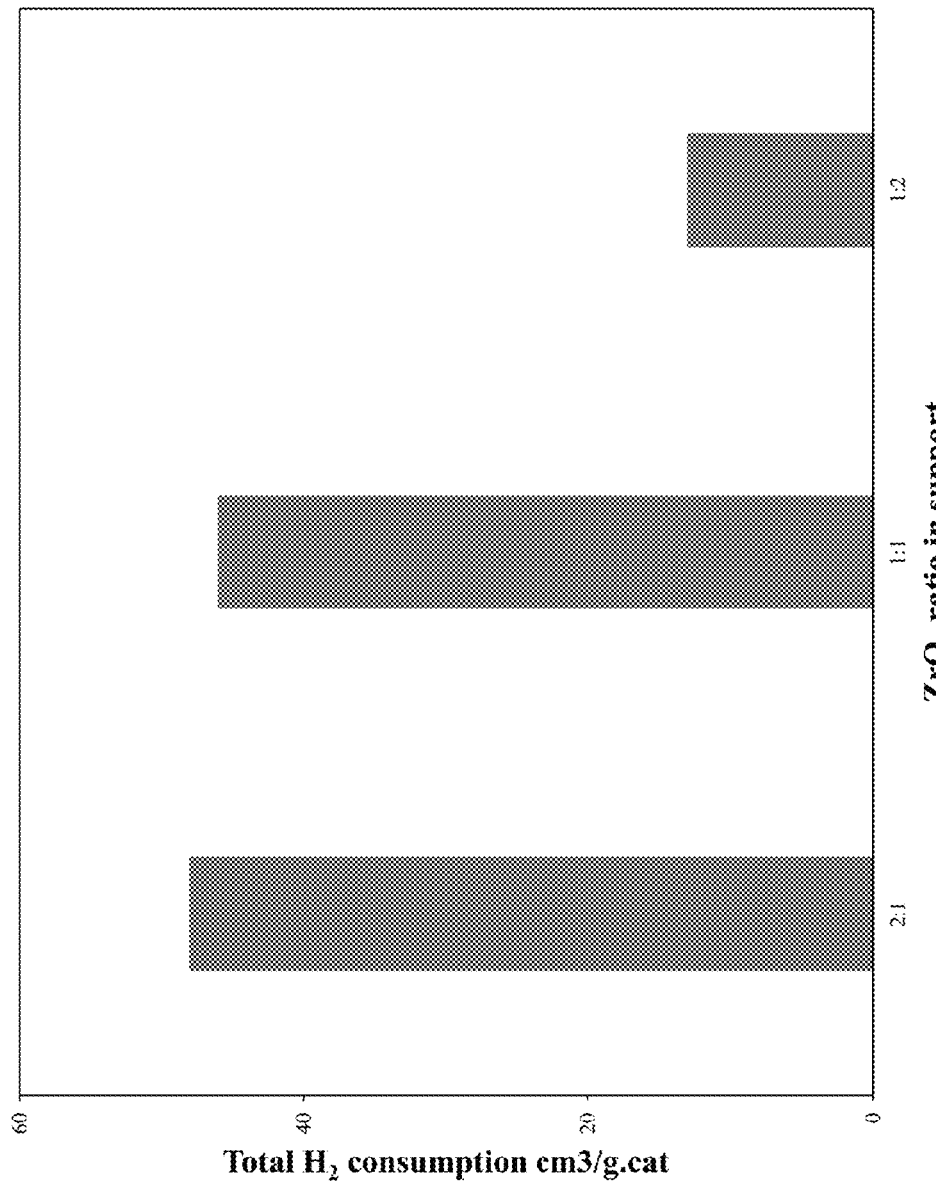
FIG. 4B shows the $H_2$ consumption of various $Al_2O_3$—$ZrO_2$ catalysts with various $ZrO_2$ loadings.

It can be seen in both Eq. 8 and Eq. 9 cases, by using hydrogen or ethane, ODH reduces the $V_2O_5$ into $V_2O_3$. Consequently, the TPR evaluation of the catalyst sample can be correlated to the activity (reactivity) of the catalyst at various temperature ranges. The TPR/TPO test also determines the oxygen-carrying capacity and the redox properties of the catalysts. The oxygen-carrying capacity eventually determines the circulation rate of the catalyst between the twins fluidized bed reactors: ODH reactor and the catalyst regenerator. FIGS. 4A and 4B show the TPR profiles and the $H_2$ consumption, for different $ZrO_2$ containing catalysts. In all samples, the V loading is kept at a 15 wt % of the catalyst. Thus, the presence of multiple peaks indicates that the reduction proceeds in several steps [F. Klose, T. Wolff, H. Lorenz, a Seidelmorgenstern, Y. Suchorski, M. Piorkowska, and H. Weiss, "Active species on γ-alumina-supported vanadia catalysts: Nature and reducibility," J. Catal., vol. 247, no. 2, pp. 176-193, April 2007; Y. H. Kim and H. Lee, "Redox Property of Vanadium Oxide and Its Behavior in Catalytic Oxidation," vol. 20, no. 12, 1999—each incorporated herein by reference in its entirety]. The introduction of the $ZrO_2$, reduced the support surface acidity, and as a result, this enhances the formation of isolated mono-vanadate species on the support surfaces [I. E. Wachs, "Catalysis science of supported vanadium oxide catalysts," Dalton Trans., vol. 42, no. 33, pp. 11762-9, September 2013; J. R. Sohn, S. G. Cho, Y. Il Pae, and S. Hayashi, "Characterization of Vanadium Oxide-Zirconia Catalyst," vol. 177, no. 0076, pp. 170-177, 1996—each incorporated herein by reference in its entirety]. During vanadium oxide reduction, oxygen vacancies are formed at the surface. As the reduction proceeds, the concentration of these vacancies gradually decreases. Vacancies may however, aggregate and part of vanadium oxide edges may produce a new structure (non-isolated species). This may also occur, as a result of increases on the vanadium loading [A. M. Elfadly, A. M. Badawi, F. Z. Yehia, Y. A. Mohamed, M. A. Betiha, and A. M. Rabie, "Selective nano alumina supported vanadium oxide catalysts for oxidative dehydrogenation of ethylbenzene to styrene using $CO_2$ as soft oxidant," Egypt. J. Pet., vol. 22, no. 3, pp. 373-380, December 2013—incorporated herein by reference in its entirety].

TPR results may also point to the catalyst oxygen-carrying capacity and the oxygen releasing rate. This is the case, since the oxygen-carrying capacity of the catalyst can be determined according to Eq. 8 (two moles of hydrogen reduce one mole of oxygen). FIG. 3B shows the histogram plots of hydrogen consumption at different $Al_2O_3$ to $ZrO_2$ ratios with same 15 wt % $VO_x$. It appears that the hydrogen consumption was comparable between the catalyst samples containing γ-$Al_2O_3$/$ZrO_2$ ratios of 2:1 and those of 1:1. However, catalyst reducibility was significantly decreased with γ-$Al_2O_3$/$ZrO_2$ ratios of 1:2.

Figure 5:
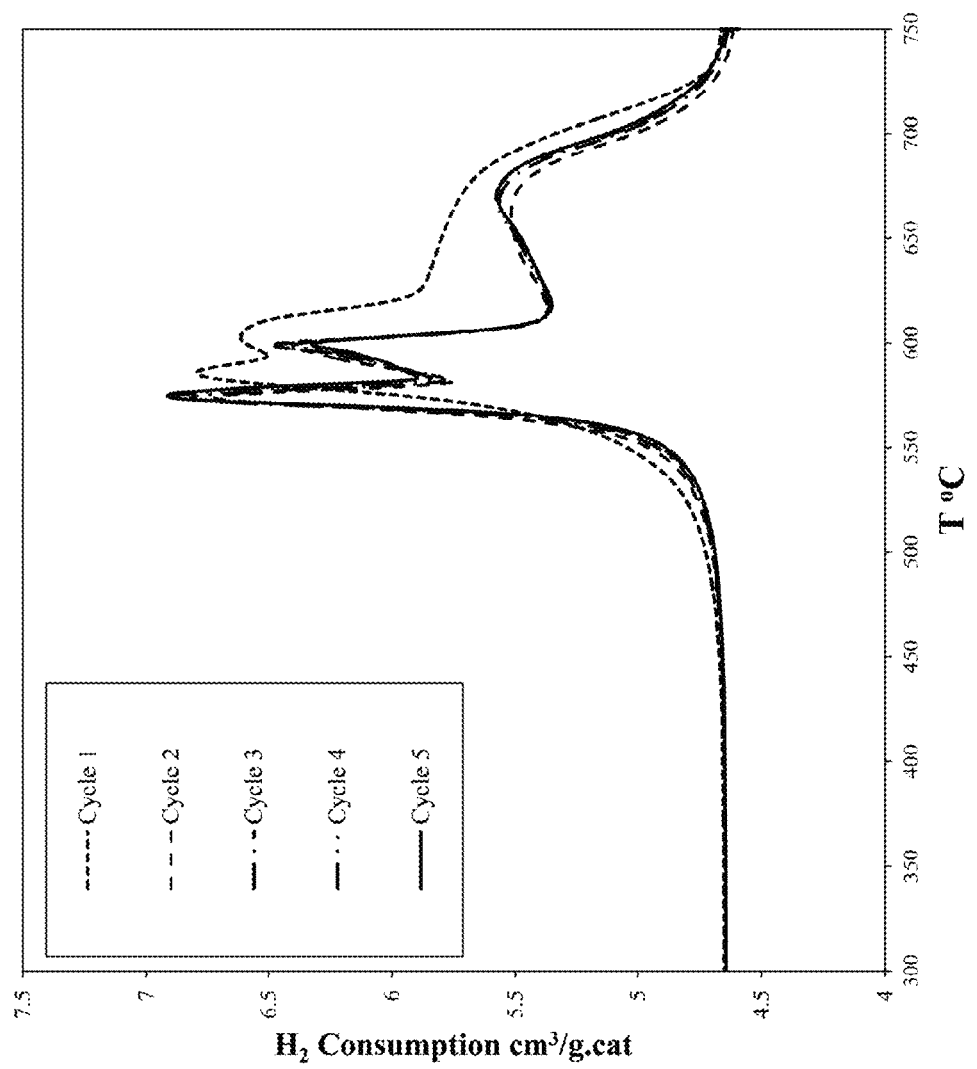
FIG. 5 shows $H_2$ consumption of TPR/TPO cycles of 15% $VO_x$/$Al_2O_3$—$ZrO_2$ (2:1) catalyst.

Repeated TPR/TPO experiments were conducted to confirm catalyst reducibility and re-oxidation ability during the multiple cycles. This also may allow considering thermal sintering in the high temperature range of the redox cycles. Regarding the $VO_x$/γ-$Al_2O_3$—$ZrO_2$ (2:1) sample, it was selected in this study due to its high oxygen-carrying capacity as revealed in hydrogen consumption analysis. FIG. 5 shows the TPR profiles for the $VO_x$/γ-$Al_2O_3$—$ZrO_2$ (2:1) sample under repeated TPR/TPO cycles. The TPR profiles remained almost unchanged during consecutive cycles with the only exception being the first cycle. It is hypothesized that it is during the first cycle that the decomposition of the residual metal precursors is completed. Once these metal precursors are removed, the hydrogen consumption became very stable over the repeated TPR/TPO cycles.

Regarding calcination temperature, it is reported that it directly affects the redox properties of supported catalysts [Y. H. Kim and H. Lee, "Redox Property of Vanadium Oxide and Its Behavior in Catalytic Oxidation," vol. 20, no. 12, 1999—incorporated herein by reference in its entirety]. However in the examples provided herein, all samples were calcined at same temperature of 750° C. which is the expected temperature of operation of the ODH in a twin fluidized bed configuration. Thus, and for the purposes of the present disclosure, only the composition of $ZrO_2$ was the parameter affecting both reduction and oxidation of the ODH catalyst, as well as poly-vanadate surface species formed. Regarding poly-vanadates, they can be formed during the reduction cycle, when oxygen vacancies are created [A. M. Elfadly, A. M. Badawi, F. Z. Yehia, Y. A. Mohamed, M. A. Betiha, and A. M. Rabie, "Selective nano alumina supported vanadium oxide catalysts for oxidative dehydrogenation of ethylbenzene to styrene using CO2 as soft oxidant," Egypt. J. Pet., vol. 22, no. 3, pp. 373-380, December 2013—incorporated herein by reference in its entirety].

Concerning the percent of vanadium reduced during redox cycles, it was calculated as given by Eq. 10:

$$\text{Fraction of Vanadium Reduced } (f)\% = \frac{Mw_v \times V_{H_2}}{v \times V_g \times W_0} \times 100\% \quad \text{(Eq. 10)}$$

where, (1) $W_v$ is the amount of reduced vanadium (g), (2) $M_{wv}$ represents the molecular weight of vanadium (g/mol), (3) $V_{H^2}$ stands for the volume of reacted hydrogen (cm$^3$ at STP), (4) $V_g$ denotes the molar volume of gas (mol/cm$^3$ at STP), (5) $W_o$ is initial weight of vanadium and v represents the stoichiometric number of hydrogen of the $VO_x$ reduction reaction ($H_2+VO_x=H_2O+V_2O_3$).

Assuming that $V_2O_5$ is the initial reducible catalyst species present on the support [S. Al-Ghamdi, M. Volpe, M. M. Hossain, and H. de Lasa, "$VO_x$/c-$Al_2O_3$ catalyst for oxidative dehydrogenation of ethane to ethylene: Desorption kinetics and catalytic activity," Appl. Catal. A Gen., vol. 450, pp. 120-130, January 2013—incorporated herein by reference in its entirety], the percent of $V_2O_5$ reduced was found to be 59% for first cycle and 57.7+/−2% for the following cycles.

Example 5

Scanning Electron Microscopy (SEM)

Shape and morphology of the active metal crystals were examined by SEM (Tescan Lyra-3) with a high performance focused ion beam (FIB) at various magnifications (up to 500 k×) using 20 kv voltage. For SEM analysis, the samples were prepared by using a 5 nm Au coating.

SEM characterization was conducted to investigate active species shape, before and after reduction in TPR. FIG. 6A is an SEM image with magnification of 50 k×, of fresh samples of $VO_x/Al_2O_3$—$ZrO_2$ (2:1) catalyst which were calcinated at 500° C. The images revealed that the impregnation of vanadium oxide resulted in non-uniform sizes and shapes of particles. The pH of the impregnation solution and the support surface affects the nature of vanadium oxide on the support. $Al_2O_3$ has a surface pH of 8.9, which results in polyvanadate formation (V—O—V bond). However, thermal treatment converts polyvanadates into monovanadates [I. E. Wachs, "Catalysis science of supported vanadium oxide catalysts," Dalton Trans., vol. 42, no. 33, pp. 11762-9, September 2013—incorporated herein by reference in its entirety]. Therefore, the fresh sample has isolated and bulk phase $VO_x$ as indicated by XRD peaks.

Figure 6B:
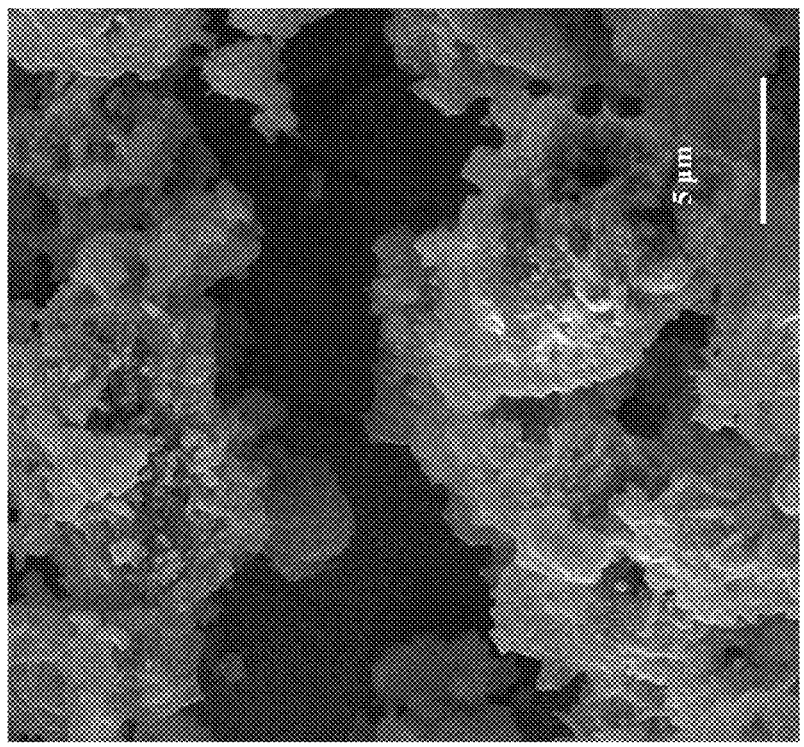
FIG. 6B is an SEM image of a TPR-reduced sample of the 15% $VO_x$/$Al_2O_3$—$ZrO_2$ (2:1) catalyst (50 k× magnification).
Figure 6A:
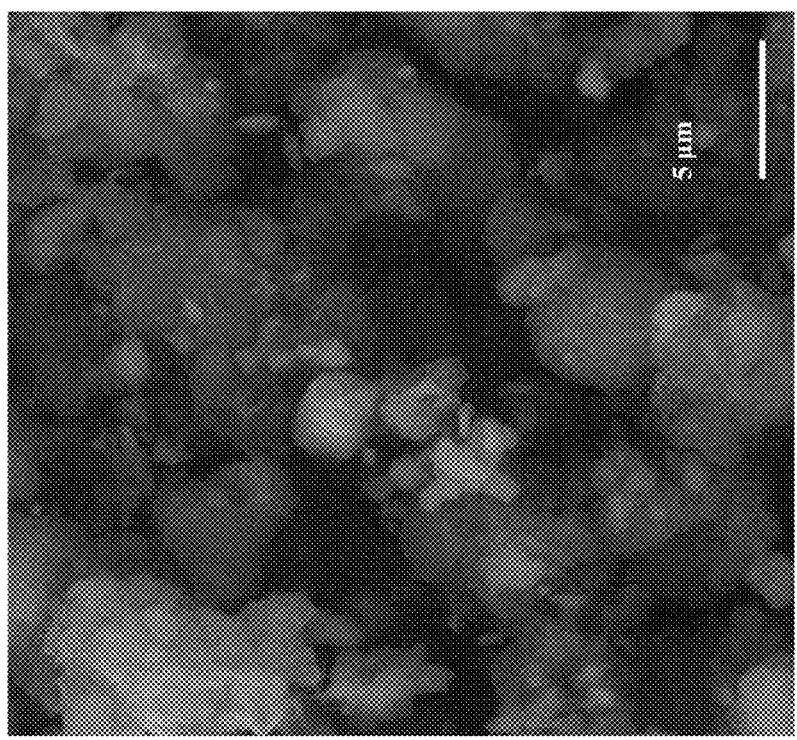
FIG. 6A is an SEM image of a fresh sample of the 15% $VO_x$/$Al_2O_3$—$ZrO_2$ (2:1) catalyst (50 k× magnification).

FIG. 6B is an SEM image for the reduced sample of $VO_x/\gamma$-$Al_2O_3$—$ZrO_2$ (2:1), which reduced at 500° C. under $H_2$ flow. Since there are many forms of $VO_x$ that can appear on the support surface, such as $V_2O_5$ and $VO_2$, these reduced oxides are mostly present in crystalline and agglomerated form.

Reduction of samples at 500° C. did not affect alumina and/or zirconia phases. However, a slight weight loss may occur, as γ-alumina tends to be modified into θ-alumina when the temperature rises to 700° C. This results in the loss of surface area. Therefore, the support can be considered stable. Similar results were concluded in open literature [Anna G. and Aftanas G., "The global approach to TPD and isothermal adsorption-desorption kinetics," Proceedings on, Tatranské Matliare (SK), 26-30 May 2003—incorporated herein by reference in its entirety]. The major change happens after the reduction of $VO_x$ on the support surface and it is reversible.

Example 6

$NH_3$ Temperature Programmed Desorption ($NH_3$-TPD)

Figure 7:
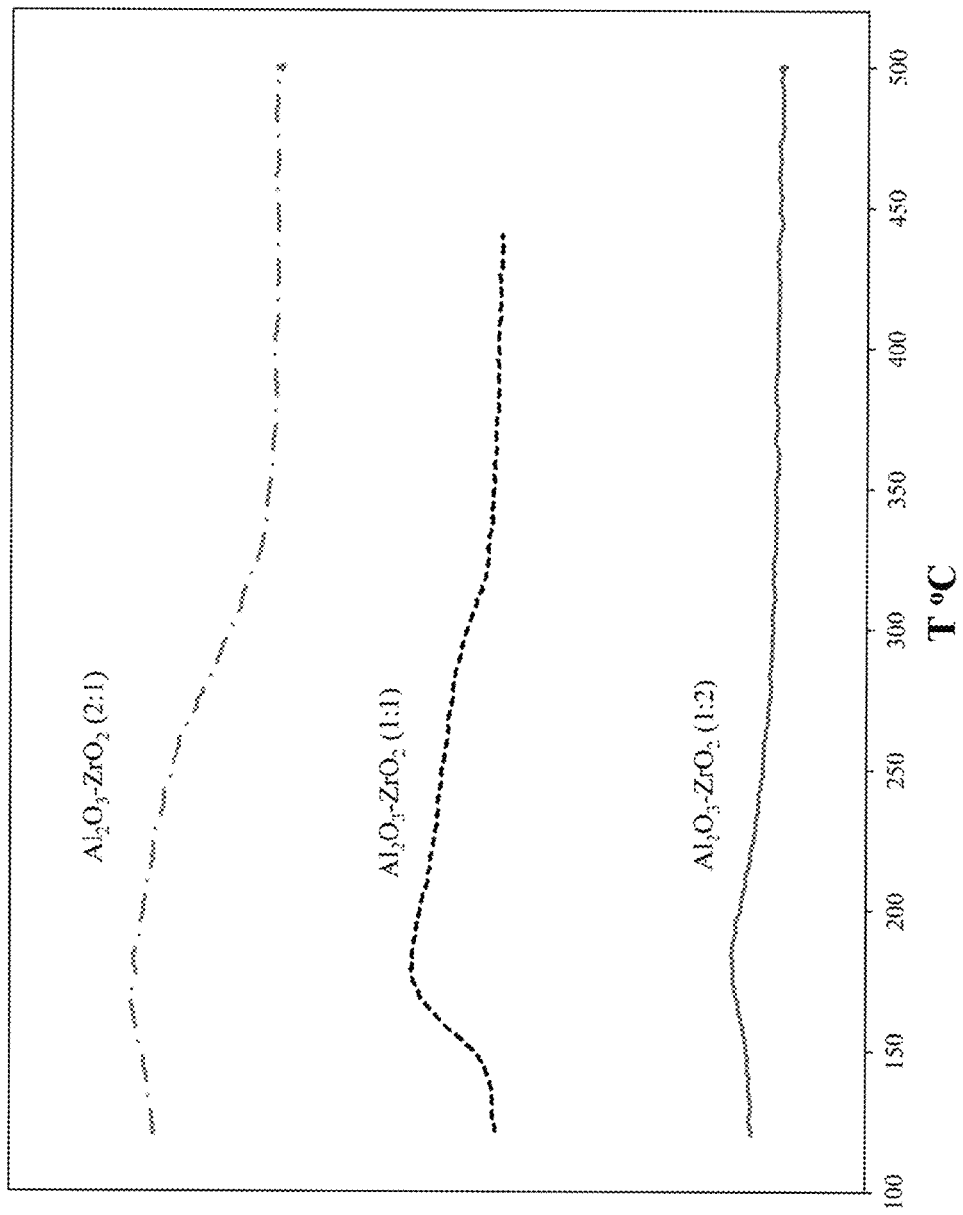
FIG. 7 shows the $NH_3$-TPD profiles of $Al_2O_3$—$ZrO_2$ support with various $ZrO_2$ loadings and 15% $VO_x$.

The purpose of the $NH_3$-TPD test was to determine catalyst total acidity as catalyst acidity affects metal-support interactions. The metal-support interactions were also evaluated by TPD kinetics analysis. Furthermore, $NH_3$-TPD was utilized to determine the quantity and strength of the acid sites available, on the surface of the prepared catalyst samples. $NH_3$-TPD experiments were conducted using a Micromeritics AutoChem II 2029 Analyzer. A catalyst sample (0.15-0.20 g) was placed in a U-shaped quartz container and degassed for 2 h at 300° C., in a flow of helium at 30 ml/min. The samples were then cooled to 120° C. and brought to saturation with ammonia (due to its strong basicity and small molecular size) using a $NH_3$/He gas mixture (5% $NH_3$/He), for one hour at a rate of 50 ml/min. Furthermore, ammonia allows one to determine the total acidity and strength of acid sites, for wide range of temperatures [R. Bulánek, P. Čičmanec, and M. Setnička, "Possibility of $VO_x/SiO_2$ Complexes Speciation: Comparative Multi-wavelength Raman and DR UV-vis Study," Phys. Procedia, vol. 44, pp. 195-205, January 2013—incorporated herein by reference in its entirety]. After that, the ammonia flow was stopped, and replaced by a He purge gas, fed at the rate of 50 ml/min. This was done for 1 h, at 120° C., to remove the physically adsorbed ammonia. Following this step, the temperature was raised up to 500° C. at different heating rates (10, 20 and 30° C./min). As the temperature was increased, the ammonia desorbed as it gained enough energy to overcome the activation energy barrier. The desorbed concentration of ammonia was recorded using a TCD detector. FIG. 7 shows the $NH_3$-TPD profiles of the catalyst samples with various $Al_2O_3/ZrO_2$ ratios. $ZrO_2$ affects metal-support interactions especially at low and intermediate metal loading [J. R. Sohn, S. G. Cho, Y. Il Pae, and S. Hayashi, "Characterization of Vanadium Oxide-Zirconia Catalyst," vol. 177, no. 0076, pp. 170-177, 1996—incorporated herein by reference in its entirety]. It can be seen from FIG. 7 that desorption profiles of the samples have not significantly changed after the $ZrO_2$ modification. Total acidity was calculated by calibrating the TCD signals to the volume of $NH_3$ desorbed and by numerical integration of the area under the TPD profile (FIG. 7). A heating rate of 10° C./min was used, and samples were weighted during TPD test. All samples weighted 0.2 g. Eq. 11 was used to calculate sample total acidity as follows:

$$\text{Total acidity (ml NH}_3\text{/g)} = \frac{a}{w\beta} \quad \text{(Eq. 11)}$$

where, a is the area under the curve after TCD signal calibration (ml $NH_3$° C./min), w represents sample weight and β stands for the heating rate ° C./min.

Sample total acidity was found to be in the range between 2 and 6 (ml$NH_3$/g.cat) as shown in Table 2. The total acidity was reduced when decreasing the $Al_2O_3/ZrO_2$ ratios (increasing the $ZrO_2$ content). Zirconia and vanadium loading diminishes samples acidity by blocking acid sites [D. Sun, R. Narita, F. Sato, Y. Yamada, and S. Sato, "Catalytic Dehydration of 1,2-Propanediol into Propanal over Ag-Modified Silica; Alumina," Chem. Lett., vol. 43, no. 4, pp.

450-452, 2014—incorporated herein by reference in its entirety]. However, increasing the $ZrO_2$ ratio decreased total acidity.

TABLE 2

Estimated[b] TPD model parameters for catalyst samples at 10° C./min heating rate.

| Sample | $K_{des, 0}$ (cm³/min) | $E_{des}$ kJ/mol | $R^2$ | $AIC^c$ | $V_{des}$ (ml $NH_3$/ g · cat) |
|---|---|---|---|---|---|
| 15% $VO_x$/ $Al_2O_3$—$ZrO_2$(2:1) | 3.9 × $10^{-6}$ | 75.44 ± 3.5 | 0.99 | −64252 | 5.87 |
| 15% $VO_x$/ $Al_2O_3$—$ZrO_2$(1:1) | 5.6 × $10^{-6}$ | 77.88 ± 3.8 | 0.99 | −64055 | 3.4 |
| 15% $VO_x$/ $Al_2O_3$—$ZrO_2$(1:2) | 14.9 × $10^{-6}$ | 80.52 ± 4 | 0.99 | −51751 | 2.75 |

[b]Confidence interval was set to be 95%
[c]Akiake information criterion

This observation suggests that $ZrO_2$ enhances vanadia species isolation on the surface of the catalyst. This creates more active sites, since $ZrO_2$ as mentioned before, has a lower acidity than alumina [S. Al-Ghamdi, M. Volpe, M. M. Hossain, and H. de Lasa, "$VO_x$/c-$Al_2O_3$ catalyst for oxidative dehydrogenation of ethane to ethylene: Desorption kinetics and catalytic activity," Appl. Catal. A Gen., vol. 450, pp. 120-130, January 2013—incorporated herein by reference in its entirety].

The $NH_3$-TPD data was further treated to estimate the desorption kinetic parameters such as the desorption energy $E_{des}$ and the frequency factor $k_{des,0}$. These kinetic parameters are very important to assess the metal-support interaction. The $NH_3$-TPD data can be modeled as described in [R. Bulánek, P. Čičmanec, and M. Setnička, "Possibility of $VO_x$/$SiO_2$ Complexes Speciation: Comparative Multi-wavelength Raman and DR UV-vis Study," Phys. Procedia, vol. 44, pp. 195-205, January 2013—incorporated herein by reference in its entirety] and used to estimate these parameters under the following assumptions:

i—Homogeneous catalyst surface, $k_d=(-E_{des}/RT)$.
ii—Ammonia does not re-adsorb during experiment.
iii—Uniform adsorbate concentration in the gas flow.
iv—First order adsorption rate in surface coverage.

A high gas flow rate was maintained to satisfy the previous assumptions. The rate of $NH_3$ desorption can be expressed as [D. Ahchieva, M. Peglow, S. Heinrich, L. Mörl, T. Wolff, and F. Klose, "Oxidative dehydrogenation of ethane in a fluidized bed membrane reactor," Appl. Catal. A Gen., vol. 296, no. 2, pp. 176-185, December 2005—incorporated herein by reference in its entirety]:

$$r_{des} = -V_m\left(\frac{d\theta_{des}}{dt}\right) = k_{d,0}\theta_{des}\exp\left[\frac{-E_{des}}{R}\left(\frac{1}{T} - \frac{1}{T_m}\right)\right] \quad (Eq.\ 12)$$

where, (1) $\theta_{des}$ is the surface coverage, (2) $k_{d,0}$ represent the pre-exponential factor, (3) $T_m$ stands for the centering temperature. By rising the temperature gradually with a constant value β, the following equations can be applied:

$$T = T_0 + \beta t \quad (Eq.\ 13)$$

$$\frac{dT}{dt} = \beta \quad (Eq.\ 14)$$

$$\left(\frac{d\theta_{des}}{dt}\right) = \left(\frac{d\theta_{des}}{dT}\right)\left(\frac{dT}{dt}\right) = \beta\left(\frac{d\theta_{des}}{dT}\right) \quad (Eq.\ 15)$$

Eq. 13 and Eq. 14 give:

$$\left(\frac{d\theta_{des}}{dt}\right) = \frac{k_{des,0}}{V_m \times \beta}\theta_{des}\exp\left[\frac{-E_{des}}{R}\left(\frac{1}{T} - \frac{1}{T_m}\right)\right] \quad (Eq.\ 16)$$

where:

$$\theta_{des} = 1 - \frac{V_{des}}{V_m} \quad (Eq.\ 17)$$

Combining Eq. 10 and Eq. 11 would result in:

$$\left(\frac{dV_{des}}{dT}\right) = \frac{k_{des,0}}{\beta}\left(1 - \frac{V_{des}}{V_m}\right)\exp\left[\frac{-E_{des}}{R}\left(\frac{1}{T} - \frac{1}{T_m}\right)\right] \quad (Eq.\ 18)$$

Eq. 18 was fitted to the experimental data using the Mathematica NonlinearModelFit built-in function at a heating rate of 10° C./min for all samples. In all experiments, ammonia pre-adsorbed at 120° C. and samples weight was 0.2 g. Parameters obtained are shown in Table 2.

The coefficient of determination $R^2$ was found to be above 0.99. In all cases, this indicates a good regression. Akaike Information Criterion (AIC) was also used as a measure of the relative quality of a statistical model to the experimental data set. In the literature, when it is used, it is reported, to give large negative values if the fit is good, this can be seen in Table 2.

As seen in Table 2, that the activation energies for the $ZrO_2$ containing samples are higher than those of the bare $Al_2O_3$ and the $VO_x$/$Al_2O_3$. This suggests a stronger interaction between vanadium species and the support [S. Al-Ghamdi, M. Volpe, M. M. Hossain, and H. de Lasa, "$VO_x$/ c-$Al_2O_3$ catalyst for oxidative dehydrogenation of ethane to ethylene: Desorption kinetics and catalytic activity," Appl. Catal. A Gen., vol. 450, pp. 120-130, January 2013— incorporated herein by reference in its entirety]. This also confirms the presence of isolated vanadium oxide species. On the other hand, vanadium species interaction may result in the formation of $VO_2$ which will lead to a lowering of the catalyst oxygen-carrying capacity [R. Bulánek, P. Čičmanec, and M. Setnička, "Possibility of $VO_x$/$SiO_2$ Complexes Speciation: Comparative Multi-wavelength Raman and DR UV-vis Study," Phys. Procedia, vol. 44, pp. 195-205, January 2013—incorporated herein by reference in its entirety]. On the whole, the intermediate interaction between active sites and supports is favorable. TPD kinetics show increased metal-support interaction, indicated by high desorption energy due to the introduction of $ZrO_2$. Higher metal-support interaction decreases the $VO_x$ reducibility. Thus, catalyst activity is consistent with TPR results. Furthermore, decreased catalyst activity can reduce conversion of ethane. However, it is expected to increase ethylene selectivity by controlling $O_2$ release.

Example 7

CREC Riser Simulator Setup

Figure 8A:
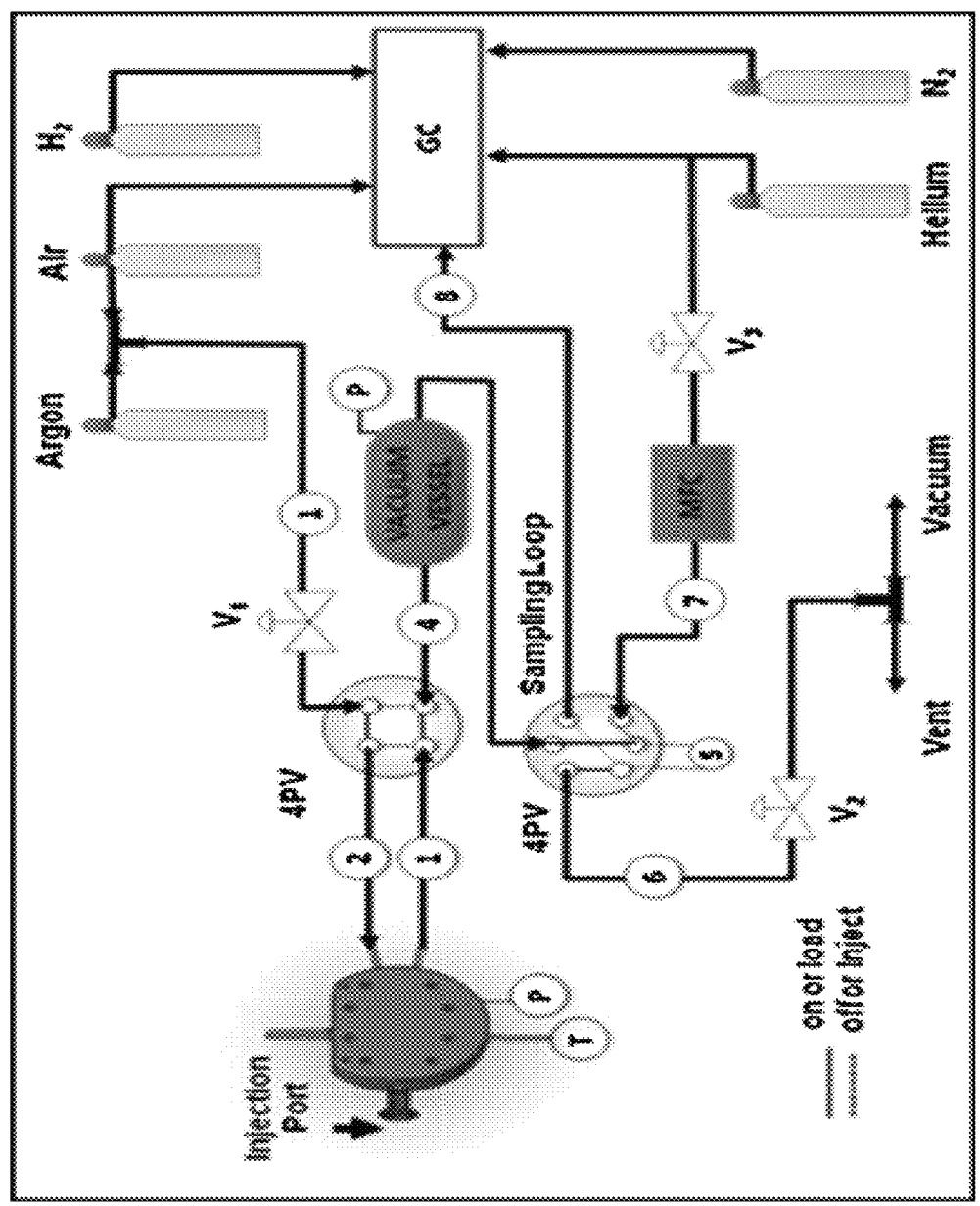
FIG. 8A is a schematic diagram of the CREC Riser Simulator experimental set-up.
Figure 8B:
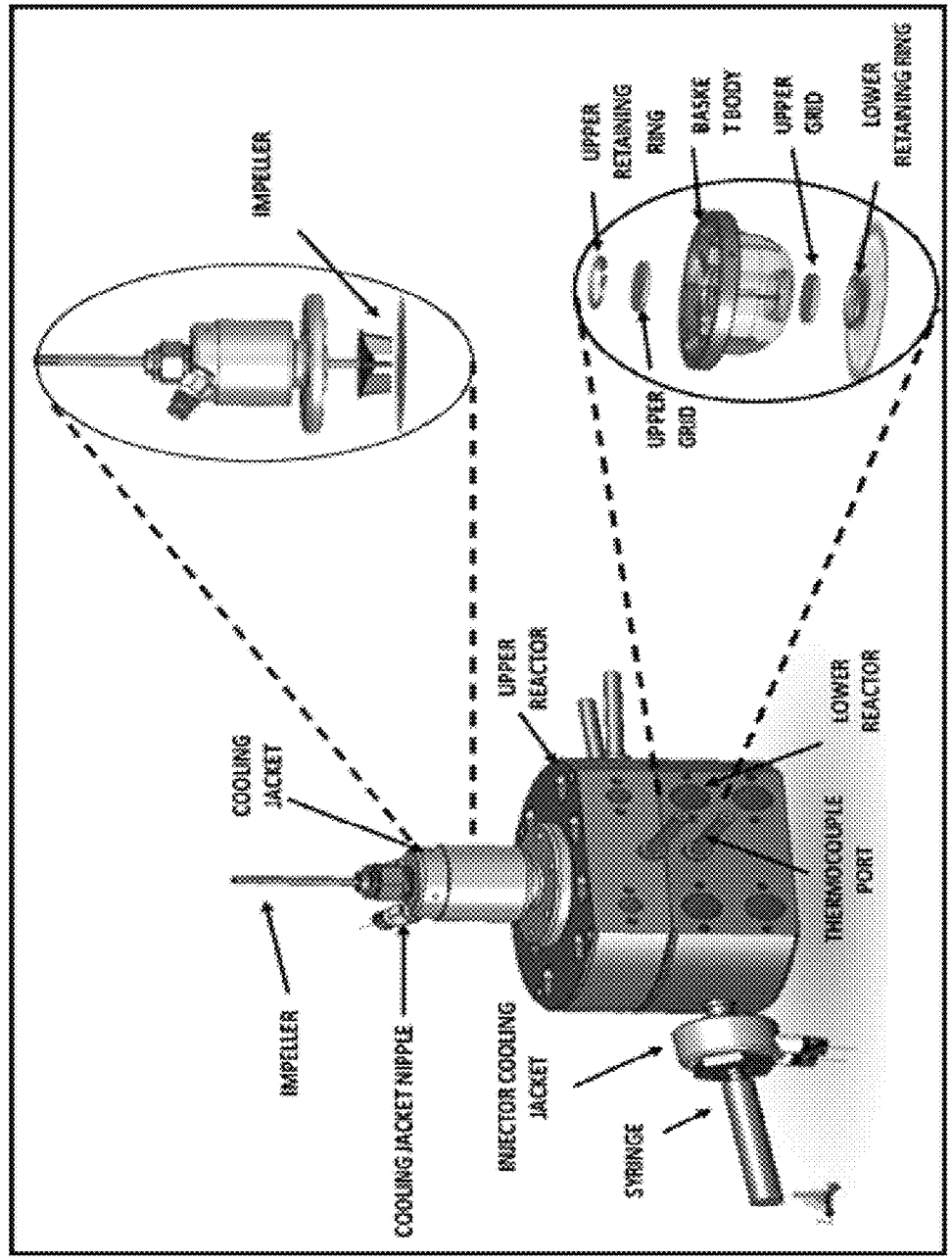
FIG. 8B is a schematic diagram providing an overview of the CREC Riser Simulator reactor body.

The reactivity and the stability of the $VO_x$/γ-$Al_2O_3$— $ZrO_2$ catalyst samples were established using a CREC Riser Simulator, whose set-up is shown in FIG. 8A [S. Al-Ghamdi, M. Volpe, M. M. Hossain, and H. de Lasa, "VO$_x$/c-Al$_2$O$_3$ catalyst for oxidative dehydrogenation of ethane to ethylene: Desorption kinetics and catalytic activity," Appl. Catal. A Gen., vol. 450, pp. 120-130, January 2013—incorporated herein by reference in its entirety]. The reactor has a capacity of 53 cm$^3$. It is a batch unit designed for catalyst evaluation and kinetic studies under fluidized bed reactor conditions. The major components of the CREC Riser Simulator are shown in FIG. 8B. These components include a vacuum box, a series of sampling valves, a timer, two pressure transducers and three temperature controllers. The product gas was analyzed by gas chromatography (GC) with a thermal conductivity detector (TCD) and a flame ionization detector (FID).

As shown in FIG. 8B, the main reactor consists of a lower shell and an upper shell. These two shells allow easy access to the reactor to load and unload catalyst samples. The lower shell houses a basket that contains the catalyst sample. The catalyst basket is bound by two grids, trapping the catalyst and restraining its mobility within this chamber. This reactor was designed in a way that an annular space is created between the outer portion of the basket and the inner part of the lower reactor shell containing the basket. This annular space facilitates the recirculation of gaseous reactants and/or products by rotation of an impeller positioned above the catalyst basket. A metallic gasket is used to seal the upper and the lower shells of the reactor. A packing gland assembly with a cooling jacket supports and seals the impeller shaft. Upon the rotation of the impeller at high speed (up to 7500 rpm), gas is forced both outward in the impeller section and downwards in the outer reactor annulus, causing the solids material (catalyst) to become fully fluidized.

Example 8

Ethane ODH Experiments

The ODH of ethane to ethylene experiments were conducted at various temperatures and contact times. The selected temperatures for the experiments were chosen to be consistent with the reduction temperatures of the catalysts, as reported in the TPR analysis.

In a typical run, 0.4 g of oxidized catalyst sample was loaded into the reactor basket and the leak test was conducted. Following the leak test, the system was purged by flowing argon. The temperature program was started to heat the reactor to the desired temperature. The argon flow was maintained to keep the reactor from any interference of gas phase oxygen. Once the reactor temperature reached to the desired temperature, the argon flow was discontinued. The reactor isolation valve was closed when it reached the desired pressure level. At this stage the vacuum pump was turned on to evacuate the vacuum box down to 20.7 kPa (3.75 psi). The catalyst was fluidized by rotating the impeller. At this point, the ethane feed was injected into the reactor by using a preloaded gas tight syringe. The reaction continued for a pre-specified time. At the termination point, the isolation valve between the reactor and vacuum box opened automatically and transferred all the reactant and products into the vacuum box. The gas samples in the vacuum bottle were analyzed using an Agilent 7890A GC equipped with both a TCD and a FID detector. For each catalytic run, the product samples were analyzed three times to ensure the accuracy of the analysis. Finally, the product analysis data were used to calculate conversion and selectivity of various products. The following definitions were used in calculating the conversion and selectivity, respectively:

$$\text{Conversion of ethane} = \frac{\text{Moles of ethane converted}}{\text{Moles of ethane fed}} \times 100\% \quad \text{(Eq. 19)}$$

$$\text{Selectivity to product} = \frac{\text{Moles of product}}{\text{Moles of ethane reacted-Moles of product}} \times 100\% \quad \text{(Eq. 20)}$$

The fluidized ODH of ethane experiments were conducted in a CREC Riser Simulator using pure ethane feed (99.95% ethane). For comparison, all three catalysts (VO$_x$/γ-Al$_2$O$_3$—ZrO$_2$) with different γ-Al$_2$O$_3$/ZrO$_2$ ratios (constant 15% VO$_x$ loading) were evaluated under same experimental conditions. The catalyst activity and product selectivity was evaluated using 0.4 g of oxidized catalysts and 2 ml of ethane injection. The product analysis of the preliminary experiments shows that C$_2$H$_6$, C$_2$H$_4$, CO$_2$ and CO are the major products of the gas phase oxygen free ODH of ethane reaction. Based on this product analysis, the following possible reactions are considered to be involved under the studied reaction conditions:

Desired reaction, ethane to ethylene: (Eq. 21)

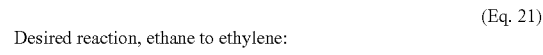

Undesired, complete oxidation of ethane: (Eq. 22)

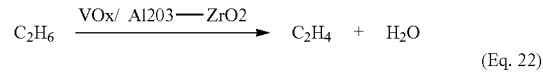
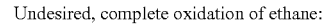

(Eq. 23)

Undesired, complete oxidation of ethylene:

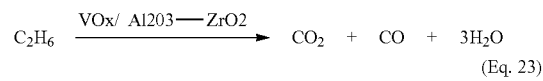
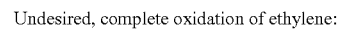
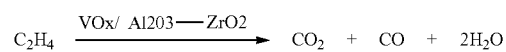

Therefore, the ODH reaction between the catalyst and the ethane feed has to be developed at the reaction conditions maximizing the desired ethylene product selectivity and minimizing complete CO$_x$ combustion.

The temperature during the experiments was varied from 525° C. to 600° C., while the contact time was adjusted between 20 and 50 s. After each ODH run, the catalyst was regenerated by supplied air at 550° C. for 10 min.

Figure 9:
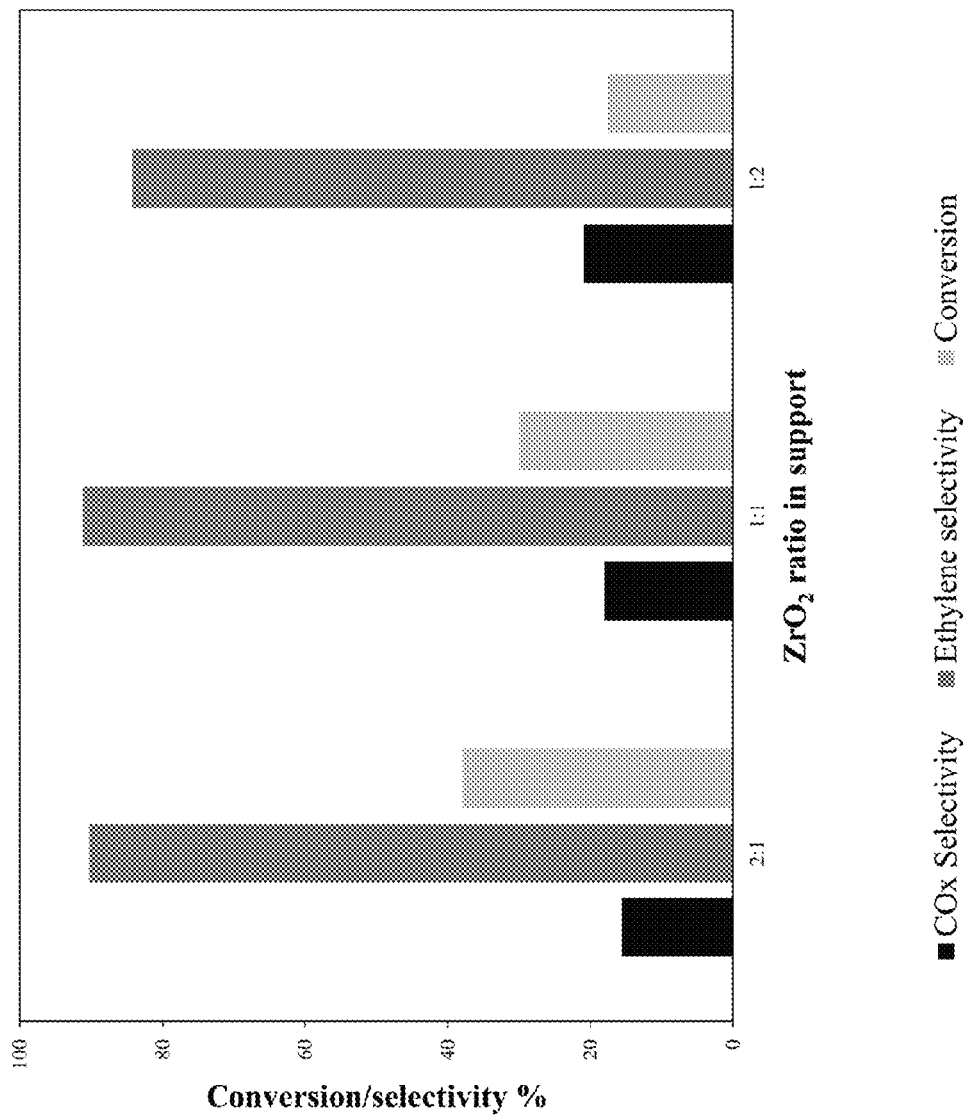
FIG. 9 shows the effect $ZrO_2$ on ethane conversion and product selectivity defined per gram $VO_x$ with reaction conditions: Reaction time=40 s, T=600° C., W=0.4, Ethane Feed=1 ml STP).

In order to demonstrate the effects of ZrO$_2$, the ethane conversion and product data are reported per gram of VO$_x$ loading on the Al$_2$O$_3$—ZrO$_2$ support basis. FIG. 9 displays the product selectivity at various Al$_2$O$_3$/ZrO$_2$ ratios. It can be noticed that all the catalyst samples studied give good selectivity to ethylene, although the highest 37.9% ethane conversion was achieved at the 2:1 γ-Al$_2$O$_3$/ZrO$_2$ ratio. The ethane conversion further decreased with the increase of the ZrO$_2$ content (decreasing γ-Al$_2$O$_3$/ZrO$_2$ ratio). This was expected after the TPR analysis of the samples, which showed that the oxygen-carrying capacity of the samples decreased with the increase of the ZrO$_2$ content on the support. Interestingly, ethane selectivity slightly increased when the γ-Al$_2$O$_3$/ZrO$_2$ ratio was decreased from 2:1 to 1:1. At these γ-Al$_2$O$_3$/ZrO$_2$ ratios, up to 90% ethylene selectivity was achieved at 600° C. Further increases of ZrO$_2$, diminished however, ethylene selectivity significantly.

On the basis of the results obtained on can conclude that overall, both the ethane conversion and ethylene selectivity were increased by augmenting the $ZrO_2$. This is due to enhanced catalyst activity via the formation of reducible poly-vanadates [E. Nouri, M. Shahmiri, H. R. Rezaie, and F. Talayian, "The effect of alumina content on the structural properties of $ZrO_2$—$Al_2O_3$ unstabilized composite nanopowders," pp. 1-8, 2012; I. E. Wachs, "Catalysis science of supported vanadium oxide catalysts," Dalton Trans., vol. 42, no. 33, pp. 11762-9, September 2013—each incorporated herein by reference in its entirety]. This agrees with the TPR results obtained as well in this study. However, at high $ZrO_2$ content, crystalline $VO_x$ species are also formed. This results in both a decreasing ethane conversion and ethylene selectivity. TPD kinetics also shows an increased metal-support interaction due to high desorption energies. This high desorption energies were likely caused by an increased surface heterogeneity, which can favor catalyst ethylene selectivity by controlling the lattice $O_2$ released [Qing Sun, Yuchuan Fu, Jingwei Liu, Aline Auroux, Jianyi Shen, "Structural, acidic and redox properties of $V_2O_5$—$TiO_2$—$SO_4^{-2}$ catalysts", Appl. Cat. A 334 (2008) 26-34—incorporated herein by reference in its entirety].

Figure 10:
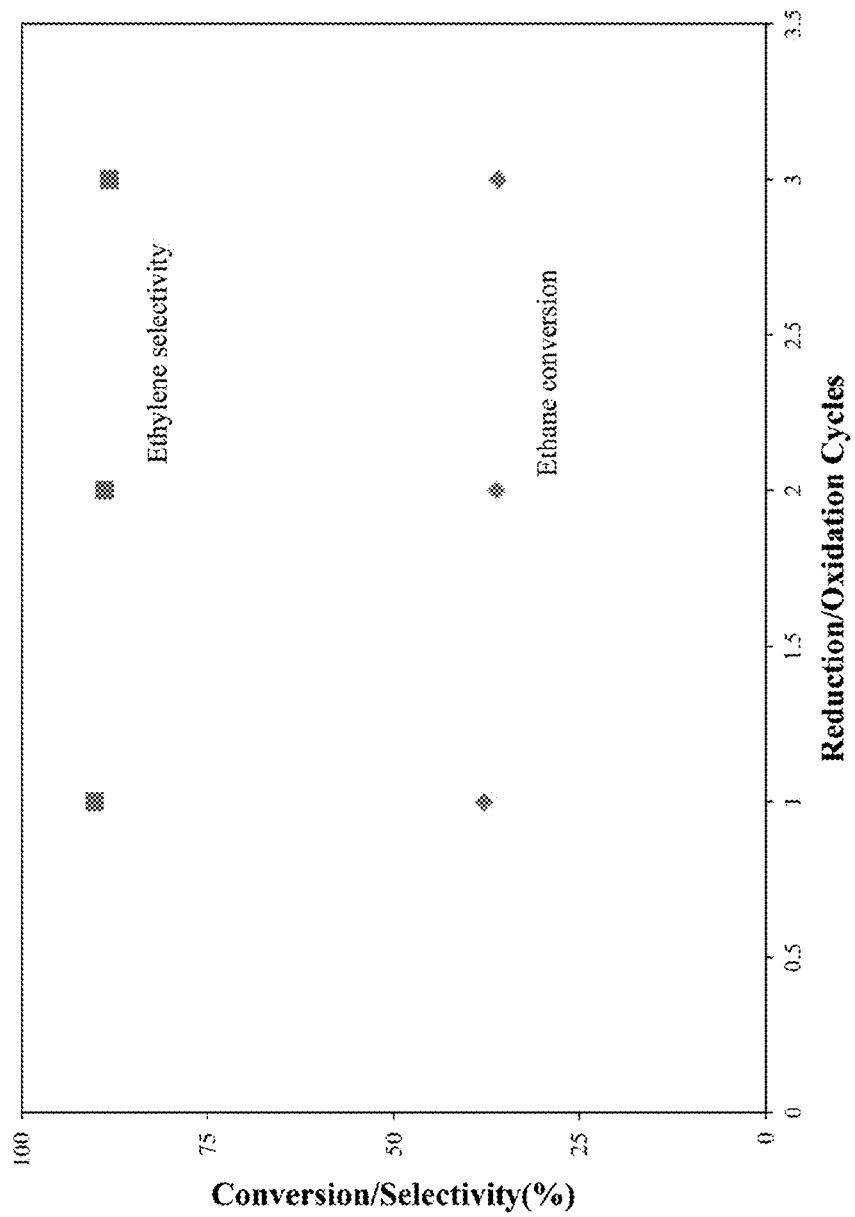
FIG. 10 shows ethane conversion and ethylene selectivity over redox cycles for the $VO_x$/$Al_2O_3$—$ZrO_2$ (2:1) catalyst, defined per gram $VO_x$ with reaction conditions: Reaction time=40 s, T=600° C., W=0.4, Ethane Feed=1 ml STP).

FIG. 10 shows ethane conversion and ethylene selectivity over three reduction and oxidation cycles for a $VO_x$/$Al_2O_3$—$ZrO_2$ (2:1) catalyst sample. Stable performance was consistently obtained, which indicates the sample thermal stability and ability to be regenerated. This observation is well in agreement with consecutive TPR/TPO data which also show a close level of reducibility during repeated reductions and oxidations.

Figure 11:
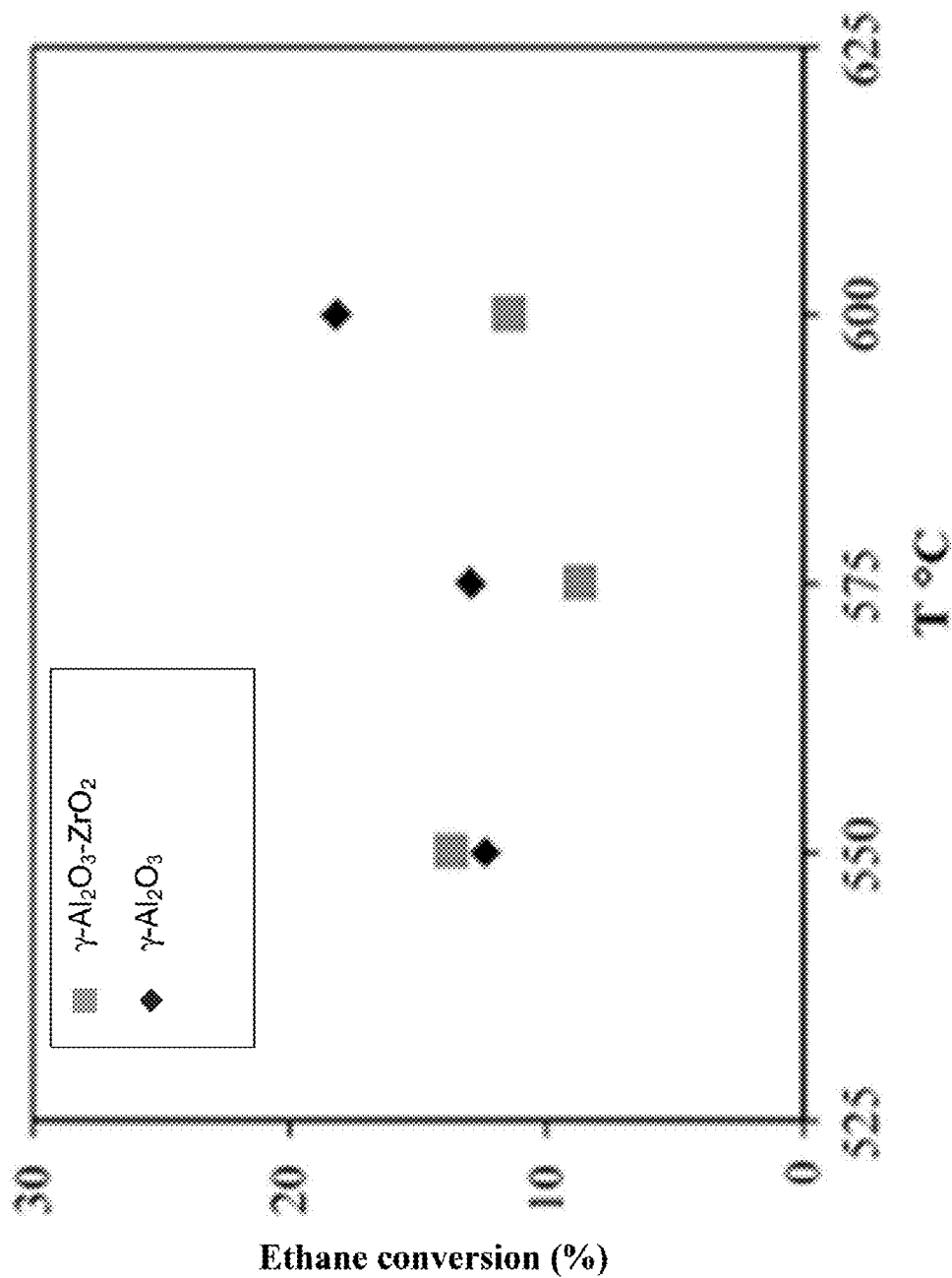
FIG. 11 shows the effect of temperature on ethane conversion, defined per gram $VO_x$ with reaction conditions: Reaction time=40 s, Ethane Feed=1 ml STP).

FIG. 11 displays the relationship between ethane conversion and ethylene selectivity with reaction temperature. It can be seen that as the reaction temperature increases, with the unprompted $VO_x$/γ-$Al_2O_3$ catalyst, the conversion of ethane is increased from 13.75% at 550° C. to 18.80% at 600° C. On the contrary, with the $VO_x$/γ-$Al_2O_3$—$ZrO_2$, the ethane conversion was slightly decreased from 13.75% at 550° C. to 11.45% at 600° C.

Figure 12:
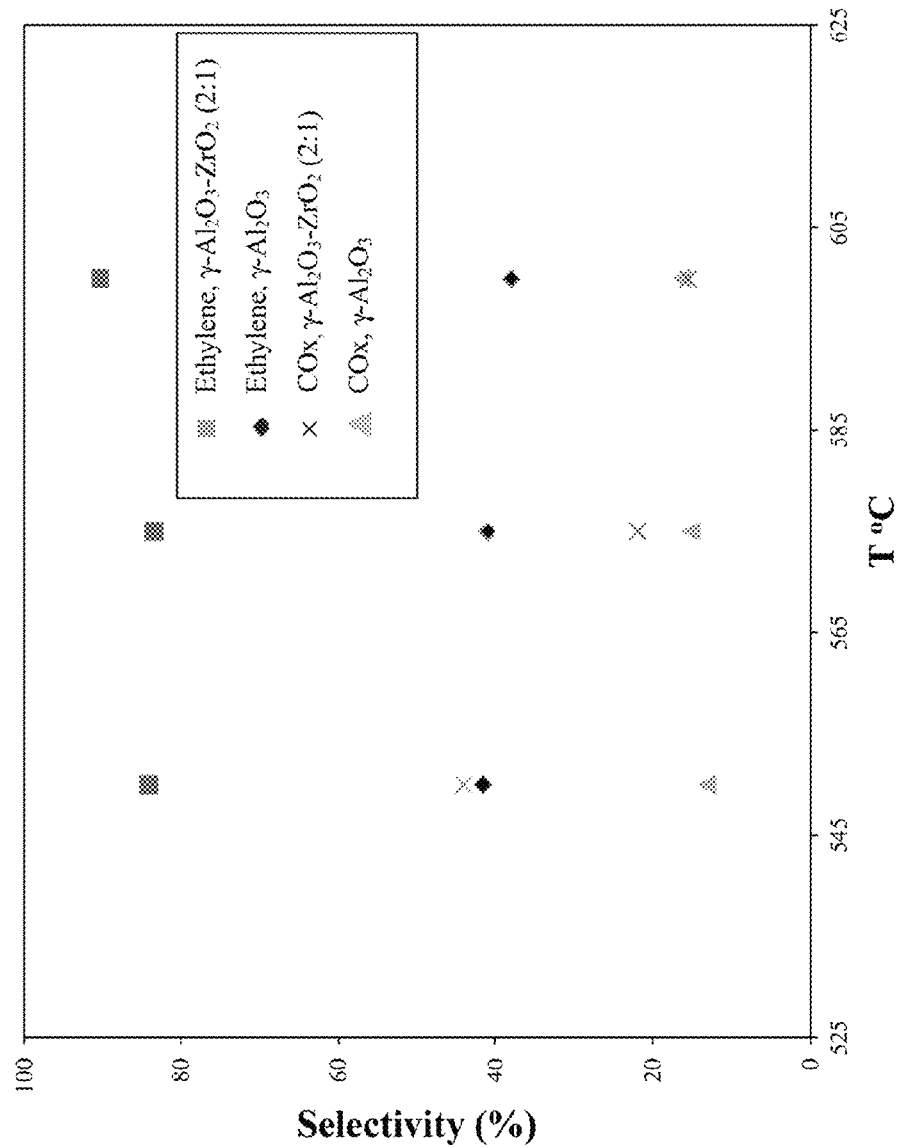
FIG. 12 shows the effect of temperature on product selectivity, defined per gram $VO_x$ with reaction conditions: Reaction time=40 s, Ethane Feed=1 ml STP).

FIG. 12 shows product selectivity when using $VO_x$/c-$Al_2O_3$ and when using $VO_x$/γ-$Al_2O_3$—$ZrO_2$ (2:1) catalyst samples. Ethylene selectivity reaches 90.3% when utilizing a $VO_x$/γ-$Al_2O_3$—$ZrO_2$ (2:1) catalyst sample and only 42% when utilizing a $VO_x$/c-$Al_2O_3$ sample. This can be attributed to the $ZrO_2$ effect, which enhances metal-support interaction, as mentioned earlier. Lower vanadium reducibility decreases $O_2$ availability for combustion reactions, consequently suppressing the formation of $CO_2$ and CO gases. Catalyst selectivity to $CO_x$ gases versus temperature is also shown in FIG. 12. The highest $CO_2$ selectivities obtained were 44.2% for a $VO_x$/γ-$Al_2O_3$—$ZrO_2$ (2:1) sample and 15.5% for a sample without $ZrO_2$.

Furthermore, in the sample containing $ZrO_2$, the formation of $CO_x$ decreased with increasing temperature, indicating the $ZrO_2$ enhanced catalyst activity and selectivity at a high temperature of 600° C. This is in agreement with TPR results as reported in FIG. 3. On the other hand, the $VO_x$/c-$Al_2O_3$ sample produced more $CO_x$ at higher temperatures which was assigned to the increased influence of complete combustion in ODH. At higher temperature, selective role of catalyst appears as removal of $H_2$ which as same as in TPR results, the selective $O_2$ comes from V-O-support bond which release this oxygen at higher temperature [R. Bulánek, P. Čičmanec, and M. Setnička, "Possibility of $VO_x$/$SiO_2$ Complexes Speciation: Comparative Multi-wavelength Raman and DR UV-vis Study," Phys. Procedia, vol. 44, pp. 195-205, January 2013—incorporated herein by reference in its entirety].

Figure 13A:
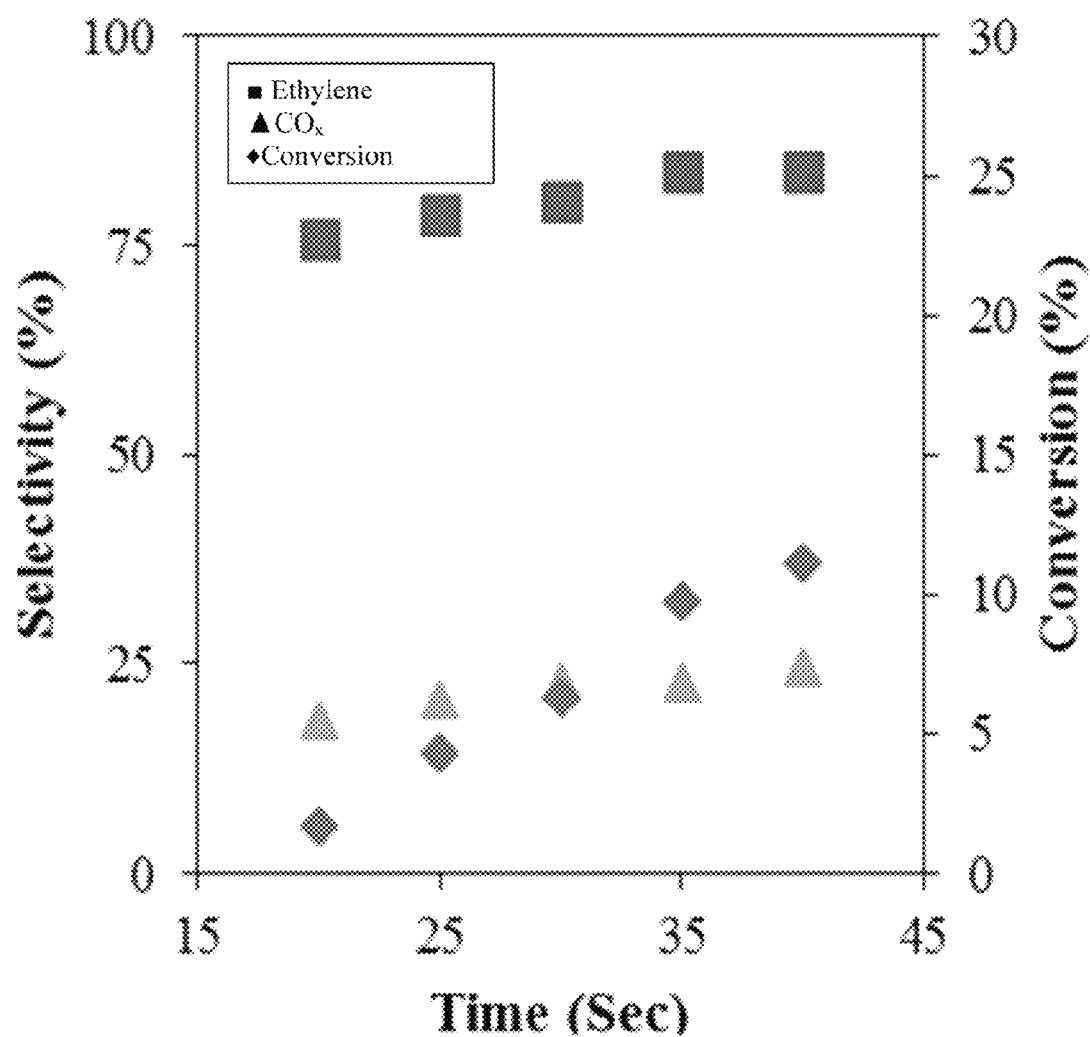
FIG. 13A shows the effect of reaction time on ethane conversion and product selectivity, defined per gram $VO_x$ loaded on $Al_2O_3$—$ZrO_2$ (2:1), with reaction conditions: T=550° C., Ethane Feed=1 ml STP).
Figure 13B:
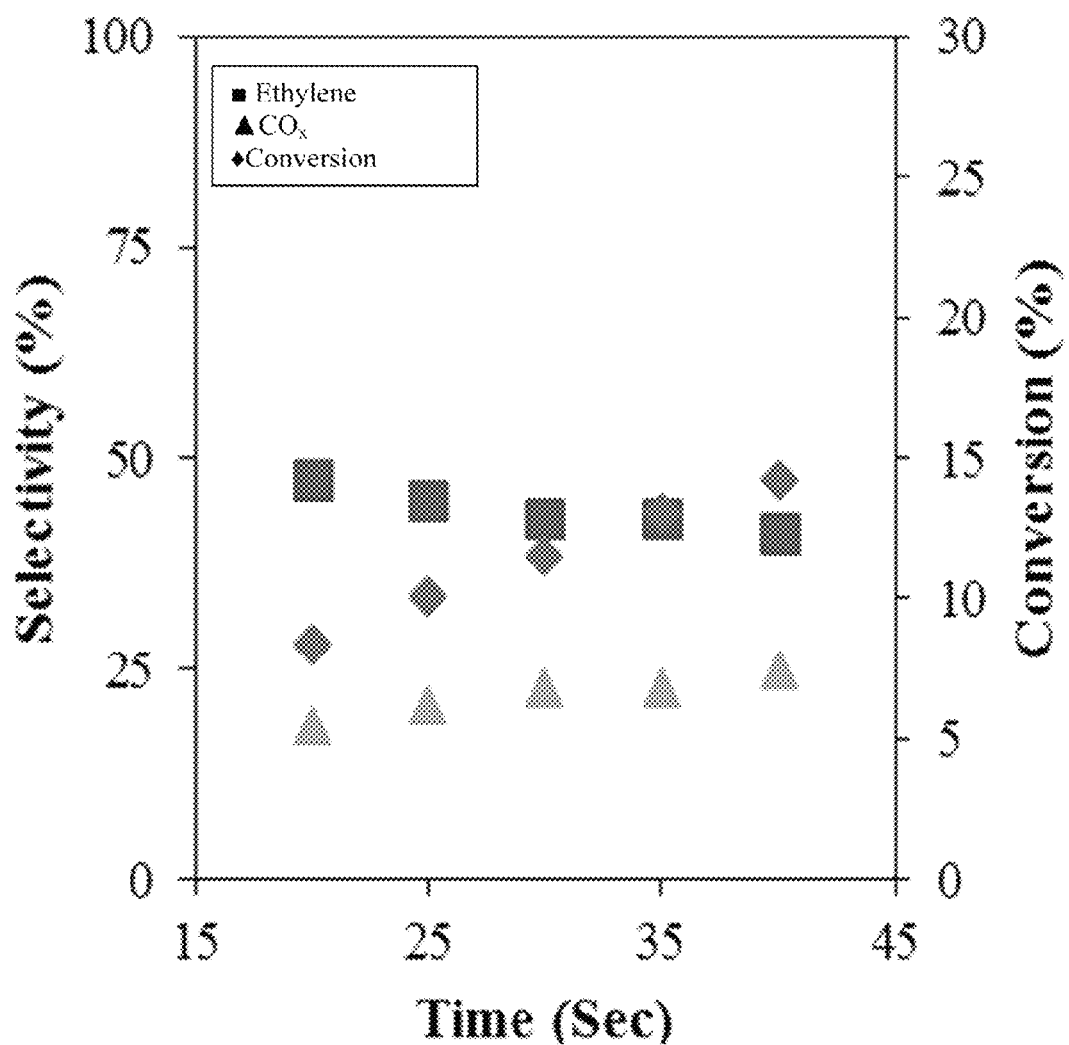
FIG. 13B shows the effect of reaction time on ethane conversion and product selectivity, defined per gram $VO_x$ loaded on $Al_2O_3$, with reaction conditions: T=550° C., Ethane Feed=1 ml STP).

The reaction time influence in the experiments in the CREC Riser Simulator at 550° C. is shown in FIGS. 13A and 13B, for both $VO_x$/γ-$Al_2O_3$—$ZrO_2$ (1:2) and $VO_x$/γ-$Al_2O_3$. In both cases, the ethane conversion augments progressively, as expected, with reaction time. Furthermore, as shown in FIG. 13A, the $ZrO_2$ addition stabilizes ethylene and $CO_x$ selectivities in the 75%-78% and 20-24% ranges respectively. These results are in significant contrast with the observations for the ODH catalyst sample without $ZrO_2$ (FIG. 13B), where selectivities to ethylene and $CO_x$ range in the 40-50% and 20-25% respectively.

Thus, it can be noticed that the introduction of $ZrO_2$ in the alumina support, enhances ethylene selectivity and stability. This is consistent with the $ZrO_2$ lowering support total acidity and also reducing Lewis acidity, as shown in $NH_3$-TPD analysis. This leads to limited cracking and $CO_x$ production. Similar results were obtained by others, when the SAPO-34 catalyst was employed in ethane ODH, where $CH_4$ traces were detected, as a result of an increased cracking influence [L. Marchese, "Acid SAPO-34 Catalysts for Oxidative Dehydrogenation of Ethane," J. Catal., vol. 208, no. 2, pp. 479-484, June 2002—incorporated herein by reference in its entirety]. Thus, it can be hypothesized that, by decreasing acidity, vanadium reducibility is mitigated. This affects both the reduction/oxidation rates, explaining the lower ethane conversions for the alumina loaded with $ZnO_2$, as shown in FIG. 13A. $ZrO_2$ enhances however the metal-support interaction leading to higher ethylene selectivity to ethylene values as a result of dehydrogenation.

It should be mentioned that as expected at a certain point of $ZrO_2$ loading, the reduction of $V_2O_5$ species become more difficult. This is shown in XRD and TPR profiles, where $VO_2$ was detected, when fresh samples were treated with $H_2$ at higher temperatures (above 500° C.). This can affect the nature of the $VO_x$ species on the support surface and the types of bonds between these species.

It was reported that the V-support interaction and the V loading, determine the type of surface bonds and thus, what type of $VO_x$ species exist on the support surface [I. E. Wachs, "Catalysis science of supported vanadium oxide catalysts," Dalton Trans., vol. 42, no. 33, pp. 11762-9, September 2013—incorporated herein by reference in its entirety]. There are several types of $VO_x$ species, such as isolated vanadium oxide species, dimeric vanadium oxide species, two-dimensional vanadium oxide chains and $V_2O_5$ crystals. $VO_x$ on different supports were reported to contain isolated, dimeric and crystalline $V_2O_5$ [R. Bulánek, P. Čičmanec, and M. Setnička, "Possibility of $VO_x$/$SiO_2$ Complexes Speciation: Comparative Multi-wavelength Raman and DR UV-vis Study," Phys. Procedia, vol. 44, pp. 195-205, January 2013—incorporated herein by reference in its entirety]. These $VO_x$ species contain V=O terminal bonds with V-O-V and V-O-support bonds. The V-O-V bond is associated with polymeric $VO_x$ species. Previous studies showed that the V-O-V has no effect in ODH reactions.

In summary, it can be stated that even if the specific details of various vanadium species formed on γ-Alumina VOx catalyst doped with $ZrO_2$ are not precisely known, it is proven that under the specified loadings of $ZrO_2$ dopant, there is a significant and valuable enhancement of ethylene selectivity for this ODH fluidizable catalyst.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A fluidizable catalyst comprising:
a zirconia-modified alumina support material; and
10-20% of one or more vanadium oxides by weight based on a total weight of the fluidizable catalyst, the one or more vanadium oxides being adsorbed onto the support material;
wherein the support material comprises an alumina/zirconia weight ratio of 1-5:1-3; and
wherein the fluidizable catalyst has an average particle size of 40-120 μm.

2. The fluidizable catalyst of claim 1, wherein the one or more vanadium oxides are selected from the group consisting of $V_2O_5$, $VO_2$, and $V_2O_3$.

3. The fluidizable catalyst of claim 2, comprising at least 50% of $V_2O_5$ based on total weight of the one or more vanadium oxides.

4. The fluidizable catalyst of claim 1, wherein the alumina/zirconia weight ratio is 1-2:1.

5. The fluidizable catalyst of claim 1, wherein the one or more vanadium oxides form a crystalline phase on the surface of the zirconia-modified alumina support material.

6. The fluidizable catalyst of claim 1, having an apparent particle density of 1.5-3.5 $g/cm^3$.

7. The fluidizable catalyst of claim 1, having Class B powder properties in accordance with Geldart particle classification.

8. The fluidizable catalyst of claim 1, wherein the zirconia present in the alumina/zirconia ratio depresses the surface acidity of the fluidizable catalyst.

9. The fluidizable catalyst of claim 1, wherein the zirconia present in the alumina/zirconia ratio enhances the interaction between the one or more vanadium oxides and the support material.

10. The fluidizable catalyst of claim 1, wherein the zirconia present in the alumina/zirconia ratio enhances the reducibility of the one or more vanadium oxides.

11. A process for converting an alkane to a corresponding olefin, comprising:
contacting an alkane feed stream with the fluidizable catalyst of claim 1 in an oxygen-free atmosphere at 525-675° C.

12. The process of claim 11, wherein the alkane is selected from the group consisting of ethane, propane, n-butane and isobutane.

13. The process of claim 11, wherein the fluidizable catalyst is present at an amount of 0.05-0.5 g/ml of the alkane feed stream.

14. The process of claim 11, wherein the alkane is ethane and the process has an ethane conversion of 15-45%.

15. The process of claim 11, wherein the alkane is ethane and the process has an ethylene selectivity of 75-90%.

16. A fluidizable catalyst, comprising:
a zirconia-modified alumina support material; and
10-20% of one or more vanadium oxides by weight based on a total weight of the fluidizable catalyst, the one or more vanadium oxides being adsorbed onto the support material;
wherein the support material comprises an aluminalzirconia weight ratio of 1-5:1-3; and
wherein the fluidizable catalyst is in the form of a plurality of particles and more than 75% of the particles have a particle size of 40-120 μm.

17. A process for converting an alkane to a corresponding olefin, comprising:
contacting an alkane feed stream with the fluidizable catalyst of claim 16 in an oxygen-free atmosphere at 525-675° C.

18. A fluidizable catalyst, comprising:
a zirconia-modified alumina support material; and
10-20% of one or more vanadium oxides by weight based on a total weight of the fluidizable catalyst, the one or more vanadium oxides being adsorbed onto the support material;
wherein the support material comprises an alumina/zirconia weight ratio of 1-5:1-3; and
wherein the fluidizable catalyst has a BET surface area of 10-50 $m^2/g$.

19. A process for converting an alkane to a corresponding olefin, comprising:
contacting an alkane feed stream with the fluidizable catalyst of claim 18 in an oxygen-free atmosphere at 525-675° C.

* * * * *